(12) United States Patent
Tezuka

(10) Patent No.: US 10,918,353 B2
(45) Date of Patent: Feb. 16, 2021

(54) RADIATION IMAGING APPARATUS, METHOD FOR CONTROLLING THE SAME, STORAGE MEDIUM, AND RADIATION IMAGING SYSTEM

(71) Applicant: CANON KABUSHIKI KAISHA, Tokyo (JP)

(72) Inventor: Shimpei Tezuka, Oyama (JP)

(73) Assignee: Canon Kabushiki Kaisha, Tokyo (JP)

( * ) Notice: Subject to any disclaimer, the term of this patent is extended or adjusted under 35 U.S.C. 154(b) by 160 days.

(21) Appl. No.: 16/296,008

(22) Filed: Mar. 7, 2019

(65) Prior Publication Data

US 2019/0282196 A1    Sep. 19, 2019

(30) Foreign Application Priority Data

Mar. 13, 2018  (JP) .............................. JP2018-045449

(51) Int. Cl.
*A61B 6/00*  (2006.01)
*G01T 3/00*  (2006.01)
*G01T 1/175*  (2006.01)

(52) U.S. Cl.
CPC .............. *A61B 6/563* (2013.01); *G01T 1/175* (2013.01); *G01T 3/006* (2013.01); *A61B 2562/222* (2013.01)

(58) Field of Classification Search
CPC ..... A61B 6/563; A61B 2562/222; A61B 6/56; A61B 6/4405; A61B 6/4233; A61B 6/46; A61B 6/542; G01T 3/006; G01T 1/175
See application file for complete search history.

(56) References Cited

U.S. PATENT DOCUMENTS

2014/0029721 A1*  1/2014  Niwa .................. G01T 1/24
378/62

FOREIGN PATENT DOCUMENTS

JP    2014-133184 A    7/2014
JP    2016-95278 A     5/2016

* cited by examiner

*Primary Examiner* — Don K Wong
(74) *Attorney, Agent, or Firm* — Canon U.S.A., Inc. IP Division

(57) ABSTRACT

A radiation imaging apparatus that communicates via wired communication with an irradiation control apparatus includes a radiation detection unit that detects incident radiation and obtains a moving image related to the radiation, and an imaging control unit that, in a first case where the wired communication is disconnected in a moving image capturing state in which the moving image is captured, performs control to set the moving image capturing state, and in a second case where the wired communication is disconnected not in the moving image capturing state and moving image capturing is set as next imaging, performs control to set a moving image standby state that is a standby state for the moving image capturing.

14 Claims, 13 Drawing Sheets

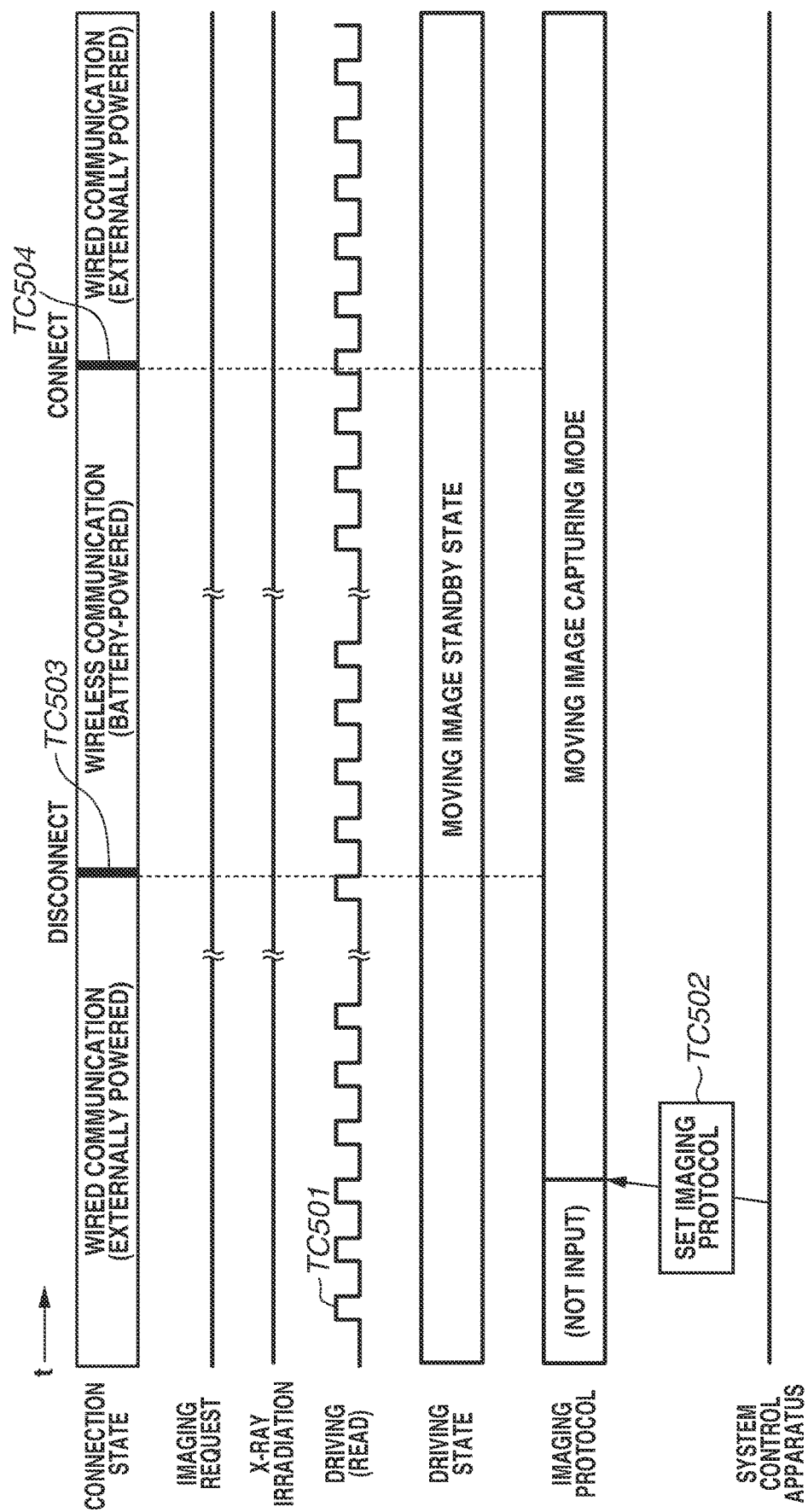

RADIATION IMAGING APPARATUS, METHOD FOR CONTROLLING THE SAME, STORAGE MEDIUM, AND RADIATION IMAGING SYSTEM

BACKGROUND

Field

The present disclosure relates to a radiation imaging apparatus that communicates with an external apparatus and a radiation imaging system including the radiation imaging apparatus and the external apparatus.

Description of the Related Art

A radiation imaging apparatus and a radiation imaging system that irradiate an object with radiation from a radiation generation apparatus, obtain a digitized radiation image of an intensity distribution of radiation transmitted through the object, and apply image processing to the radiation image to obtain a clear radiation image have been commercialized.

In such a radiation imaging system, the radiation generation apparatus emits radiation and the radiation imaging apparatus transfers the obtained radiation image data to a control apparatus, such as a control computer, for medical image diagnosis or archiving. Highly-portable radiation imaging apparatuses requiring no cable connection have recently been put into practical use. Such radiation imaging apparatuses transfer digital radiation image data to a control apparatus by using wireless communication, and include a rechargeable battery.

Wireless communication typically has low transfer rate, compared to cable-connected wired communication. For example, a moving image captured at 30 frames per second is difficult to transfer to the control apparatus in real time by using wireless communication. Portable radiation imaging apparatuses using wireless communication are therefore often configured to be limited mainly to still image capturing and low-speed moving image capturing.

In regard to this point, for example, Japanese Patent Application Laid-Open No. 2014-133184 discusses a radiation imaging apparatus that, if cable-connected, enables high-speed moving image capturing by using wired communication, and if the cable is disconnected, enables still image capturing and moving image capturing at speed lower than that with wired connection, by using wireless communication.

A radiation imaging apparatus includes a sensor array in which pixels for detecting radiation are formed in an array. Each pixel generates a certain amount of charge (hereinafter, dark charge) even when not irradiated with radiation. Dark charges are superposed on signal charges based on radiation irradiation and cause an uneven artifact on the radiation image. Dark charges vary in magnitude with the temperature of the sensor array and the time to accumulate charges. Accordingly, different artifacts occur depending on temperature variations of the sensor array and variations in accumulation time.

On this point, for example, Japanese Patent Application Laid-Open No. 2016-95278 discusses a technique for performing a moving image standby operation of stably generating additional heat even when not in charge reading operations to reduce temperature variation components when the frame rate changes. Such a radiation imaging apparatus can prevent deterioration in image quality due to a change in frame rate. To reduce the change of an artifact due to variations in charge accumulation time, charge accumulation and reading driving may desirably be continued even during the moving image standby operation at the same cycles as during moving image capturing The technique discussed in Japanese Patent Application Laid-Open No. 2016-95278 does not address a case of operating a radiation detection unit including a sensor array by an internal battery. More specifically, that the moving image standby operation of generating additional heat can shorten possible imaging time if the radiation imaging apparatus is equipped with a limited power supply such as a battery.

If the radiation imaging apparatus can operate on power supplied from an externa apparatus by cable connection, for example, the cable connection enables a stable moving image capturing operation. When the cable is disconnected, the consumption of the battery can be suppressed by switching to operation with lower power consumption.

With such operation, however, the radiation imaging apparatus is switched to a power saving standby operation once the cable is disconnected. There has thus been an issue that it takes some time for the radiation imaging apparatus to become capable of stable moving image capturing when the cable is connected again. For example, if the radiation imaging apparatus connected in a table tray in a wired manner is temporarily detached, moved to another stand or mobile visiting vehicle, and reconnected in a wired manner for moving image capturing, the moving image capturing is not always able to be immediately performed at the destination.

According to the technique discussed in Japanese Patent Application Laid-Open No. 2014-133184, high-speed moving image capturing by using wired communication is stopped when the cable connection is unintentionally disconnected during the moving image capturing by using the wired communication. In a case of moving image capturing requiring a series of a predetermined number of pieces of image data like tomosynthesis, image data obtained halfway can be unusable and the imaging needs to be performed again from the beginning. This can result in ineffective radiation irradiation.

SUMMARY

The present disclosure is directed to a mechanism that appropriately performs subsequent moving image capturing in a case where wired communication of a radiation imaging apparatus with an external apparatus is temporarily or unintentionally disconnected.

According to an aspect of the present disclosure, a radiation imaging apparatus configured to perform wired communication with an external apparatus, includes a radiation detection unit configured to detect incident radiation and obtain a moving image related to the radiation, and an imaging control unit configured to perform control to, in a first case where the wired communication is disconnected in a moving image capturing state in which the moving image is captured, set the moving image capturing state, and in a second case where the wired communication is disconnected not in the moving image capturing state and moving image capturing is set as next imaging, set a moving image standby state, the moving image standby state being a standby state for the moving image capturing.

According to other aspects of the present disclosure a method for controlling the above-described radiation imaging apparatus, a program for causing a computer to perform the control method, and a radiation imaging system including the above-described radiation imaging apparatus and the external apparatus are provided.

Further features will become apparent from the following description of exemplary embodiments with reference to the attached drawings.

BRIEF DESCRIPTION OF THE DRAWINGS

FIG. 13 is a timing chart illustrating an example of a processing procedure of a control method of the radiation imaging apparatus according to the fifth exemplary embodiment.

DESCRIPTION OF THE EMBODIMENTS

Figure 1:
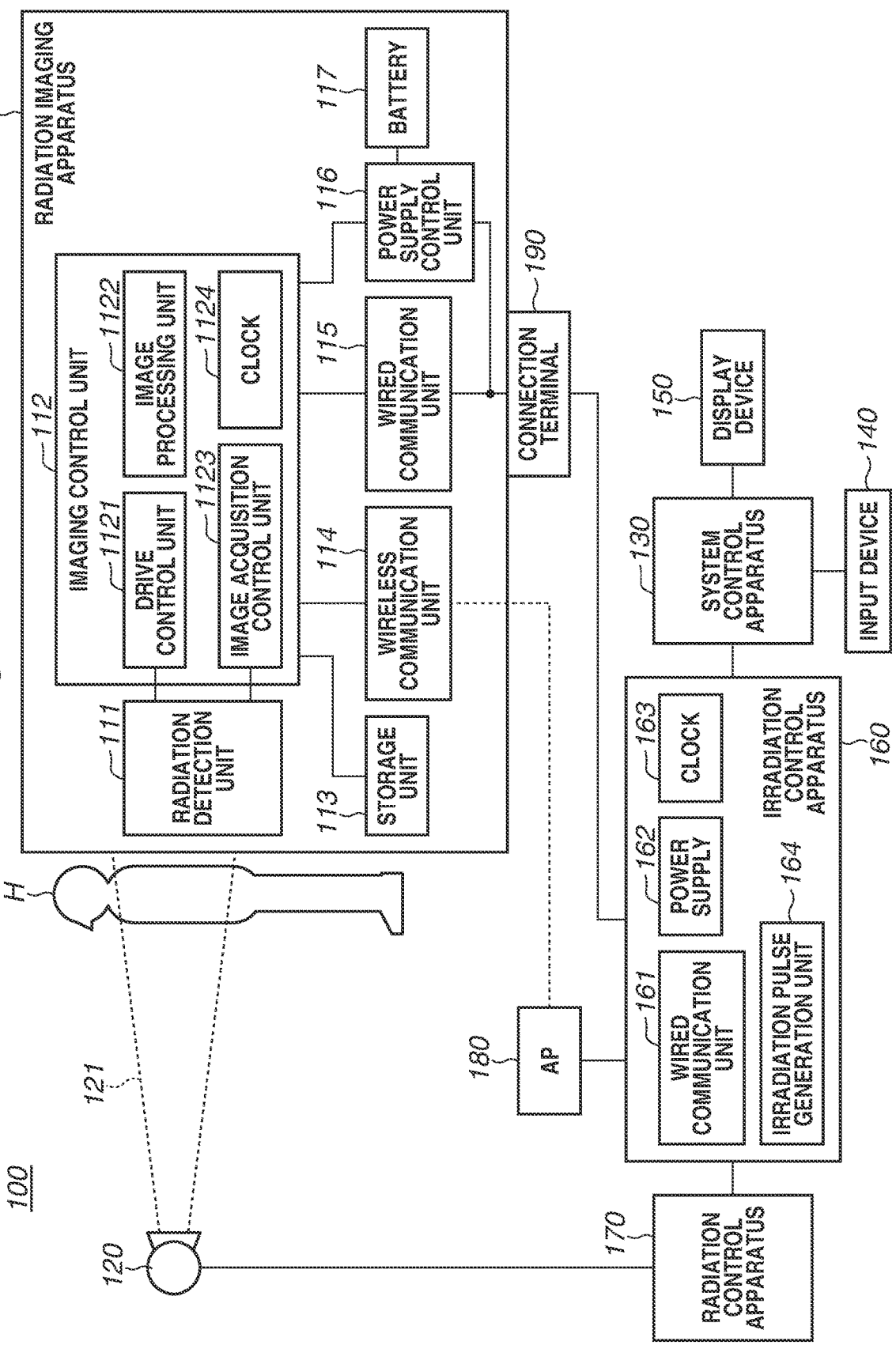
FIG. 1 is a block diagram illustrating an example of a schematic configuration of a radiation imaging system according to a first exemplary embodiment.

Exemplary embodiments will be described below with reference to the drawings. Numerical values and structural details described in the following exemplary embodiments are not limited to what are described herein and illustrated in the drawings. In addition, radiation include not only X-rays but $\alpha$-, $\beta$-, and $\gamma$-rays, and various particle beams as well.

A first exemplary embodiment will be described.

FIG. 1 is a block diagram illustrating an example of a schematic configuration of a radiation imaging system 100 according to the first exemplary embodiment. As illustrated in FIG. 1, the radiation imaging system 100 includes a radiation imaging apparatus 110, a radiation generation apparatus 120, a system control apparatus 130, an input device 140, a display device 150, an irradiation control apparatus 160, a radiation control apparatus 170, an access point (AP) 180, and a connection terminal 190.

The radiation imaging apparatus 110 communicates with the irradiation control apparatus 160, which is an external apparatus. More specifically, the radiation imaging apparatus 110 is configured perform wired communication with the irradiation control apparatus 160, which is an external apparatus, via the connection terminal 190. The radiation imaging apparatus 110 is also configured perform wireless communication with the irradiation control apparatus 160, which is an external apparatus, via the AP 180. As illustrated in FIG. 1, the radiation imaging apparatus 110 includes a radiation detection unit 111, an imaging control unit 112, a storage unit 113, a wireless communication unit 114, a wired communication unit 115, a power supply control unit 116, and a battery 117.

The radiation detection unit 111 detects radiation (including radiation transmitted through an object H) 121 emitted from the radiation generation apparatus 120 and obtains a radiation image of the object H. At this time, the radiation detection unit 111 can obtain a still image and a moving image as the radiation image. For example, a flat panel detector is suitably used as the radiation detection unit 111.

The imaging control unit 112 performs various controls related to the radiation imaging of the radiation imaging apparatus 110. The imaging control unit 112 includes a drive control unit 1121, an image acquisition control unit 1123, an image processing unit 1122, and a clock 1124. The drive control unit 1121 performs drive control on the radiation detection unit 111. The image acquisition control unit 1123 performs control to obtain a radiation image from the radiation detection unit 111. The image processing unit 1122 performs various types of image processing on the obtained radiation image. The clock 1124 performs time measuring. The imaging control unit 112 also performs control for storing the radiation image in the storage unit 113, and control for transferring the radiation image to the irradiation control apparatus 160 via the wireless communication unit 114 and the wired communication unit 115. For example, the drive control unit 1121 sets driving timing and driving conditions of the radiation detection unit 111 as the drive control on the radiation detection unit 111. For example, the image processing unit 1122 performs correction processing for correcting defects and an offset of the radiation image, and image processing including processing for reducing various types of noise. For example, the image acquisition control unit 1123 controls the storage and transfer of the obtained radiation image.

The storage unit 113 stores a program for controlling operation of the radiation imaging apparatus 110, and various types of information and various types of data required for the control. For example, the storage unit 113 stores various types of information and various types of data obtained by the processing of the imaging control unit 112. For example, the storage unit 113 stores radiation image data obtained by the imaging control unit 112 based on control of the imaging control unit 112.

The wireless communication unit 114 performs wireless communication using, for example, a wireless local area network (LAN) with the irradiation control apparatus 160 via the AP 180. The wired communication unit 115 performs wired communication using a cable with the irradiation control apparatus 160 via the connection terminal 190. For example, the imaging control unit 112 performs command communication, X-ray synchronization control communication, and image data communication with the irradiation control apparatus 160 by using one or both of the wireless communication unit 114 and the wired communication unit 115. The imaging control unit 112 detects whether a cable is connected by the connection terminal 190, and determines whether the wired communication with the irradiation control apparatus 160 is connected or disconnected. While FIG. 1 illustrates wireless communication via the AP 180, the radiation imaging apparatus 110 or the irradiation control apparatus 160 can serve as an AP to perform direct wireless communication. Wireless communication can be performed via other communication means such as a Bluetooth® wireless communication. Examples of the wired communication between the radiation imaging apparatus 110 and the irradiation control apparatus 160 via the connection terminal 190 can include Ethernet-based wired communication.

The power supply control unit 116 controls power supply to the components of the radiation imaging apparatus 110, such as the radiation detection unit 111 and the imaging control unit 112, based on control of the imaging control unit 112. The battery 117 is a power supply provided inside the radiation imaging apparatus 110. For example, if the wired communication is not disconnected (wired communication is established (connected)), the power supply control unit 116 performs control to supply power to the components of the radiation imaging apparatus 110 by using a power supply 162 of the irradiation control apparatus 160 that is an external apparatus and operate the components. If the wired communication is disconnected, the power supply control unit 116 performs control to supply power to the components of the radiation imaging apparatus 110 by using the battery 117 provided inside the radiation imaging apparatus 110 and operate the components. In the present exemplary embodiment, the battery 117 is provided inside the radiation imaging apparatus 110. However, the battery 117 can be configured to be attachable to and detachable from the radiation imaging apparatus 110, for example. The battery 117 according to the present exemplary embodiment can be one rechargeable by receiving power supply from outside, or one configured as a capacitor.

The radiation generation apparatus 120 is an apparatus that generates radiation 121 such as X-rays. For example, the radiation generation apparatus 120 includes an electron gun and a rotor. In such a case, electrons accelerated by a high voltage generated by the radiation control apparatus 170 collide with the rotor to generate the radiation 121.

The system control apparatus 130 is an apparatus that controls operation of the radiation imaging system 100 in a centralized manner For example, the system control apparatus 130 controls the operation of the radiation imaging system 100 and the acquisition and setting of an imaging protocol, and performs various controls on data processing of radiation images captured by the radiation imaging apparatus 110. For example, various types of computers and workstations can be suitably used as the system control apparatus 130. The display device 150, such as a display, and the input device 140, such as a mouse and a keyboard, are connected to the system control apparatus 130. The display device 150 is intended to display information about a control menu, as well as captured radiation images. The input device 140 is intended to make various inputs.

The irradiation control apparatus 160 functions as an interface apparatus connected to the radiation imaging apparatus 110, the system control apparatus 130, and the radiation control apparatus 170. The irradiation control apparatus 160 performs control to synchronize image acquisition timing of the radiation imaging apparatus 110 with X-ray irradiation timing of the radiation control apparatus 170. The irradiation control apparatus 160 is connected to the system control apparatus 130 by using an Ethernet network, and also functions as a relay apparatus in transferring radiation image data obtained by the radiation imaging apparatus 110 to the system control apparatus 130. The irradiation control apparatus 160 includes a wired communication unit 161, the power supply 162, a clock 163, and an irradiation pulse generation unit 164. The wired communication unit 161 performs wired communication with the radiation imaging apparatus 110. The power supply 162 enables power supply to the radiation imaging apparatus 110. The clock 163 performs time measuring. The irradiation pulse generation unit 164 issues an irradiation request to the radiation control apparatus 170.

The radiation control apparatus 170 controls the radiation 121 to be generated from the radiation generation apparatus 120. For example, a switch for requesting radiation imaging and an operation unit for setting a radiation irradiation condition can be connected to the radiation control apparatus 170. Examples of the switch include an exposure button and a fluoroscopy pedal.

Next, an internal configuration of the radiation detection unit 111 illustrated in FIG. 1 will be described.

Figure 2:
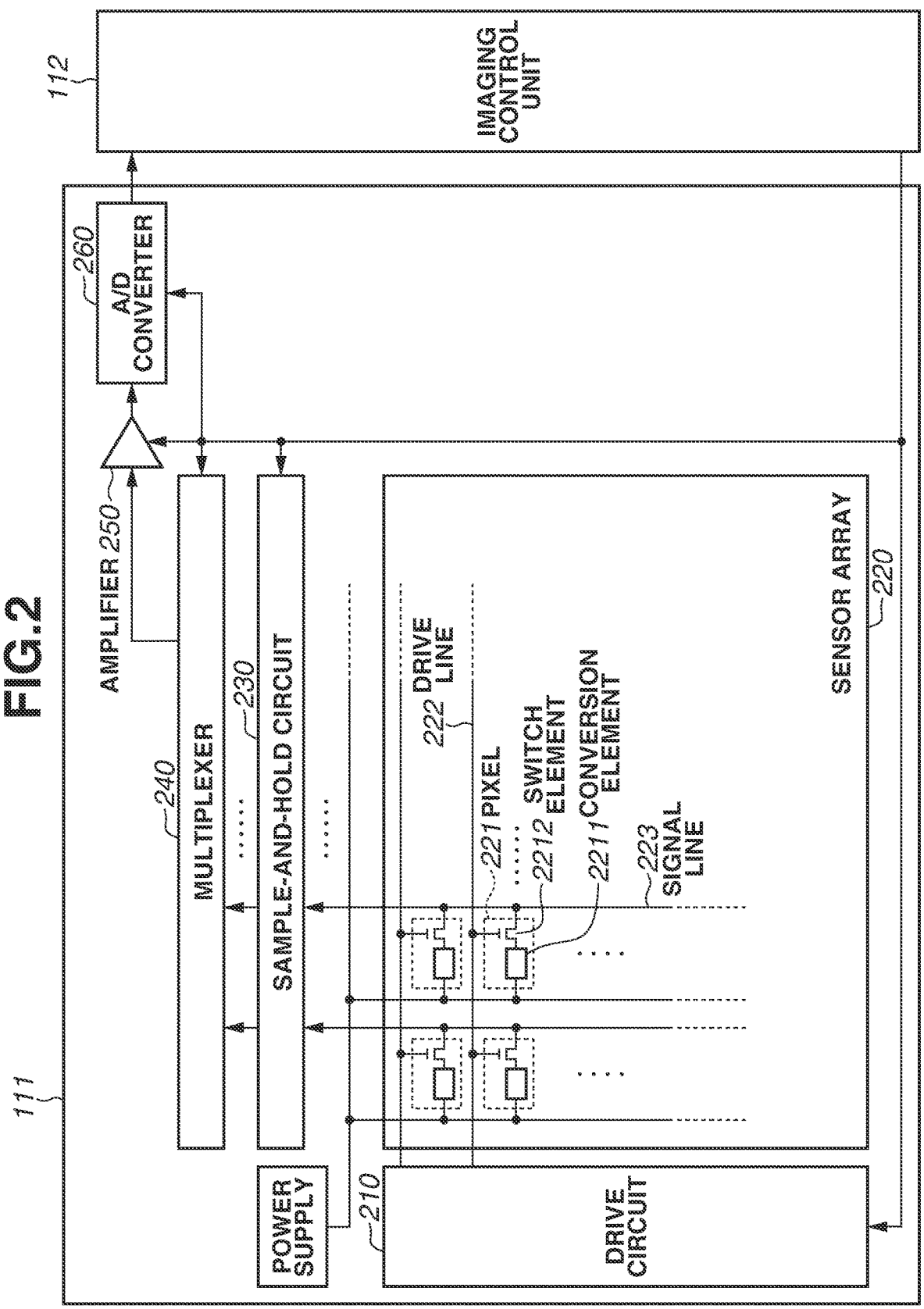
FIG. 2 is a block diagram illustrating an example of an internal configuration of a radiation detection unit illustrated in FIG. 1.

FIG. 2 is a block diagram illustrating an example of an internal configuration of the radiation detection unit 111 illustrated in FIG. 1. As illustrated in FIG. 2, the radiation detection unit 111 includes a drive circuit 210, a sensor array 220, a sample-and-hold circuit 230, a multiplexer 240, an amplifier 250, and an analog-to-digital (A/D) converter 260.

The drive circuit 210 drives a plurality of pixels 221 arranged in the sensor array 220 based on control of the imaging control unit 112.

The sensor array 220 includes the plurality of pixels 221. More specifically, the plurality of pixels 221 is arranged in the sensor array 220 in a two-dimensional array to constitute a plurality of rows and a plurality of columns.

Each pixel 221 includes a conversion element 2211 that converts incident radiation 121 into a signal charge (electrical signal), and a switch element 2212 that transfers the electrical signal to outside. An example of the switch element 2212 is a thin film transistor (TFT).

In the present exemplary embodiment, the conversion element 2211 includes a scintillator (phosphor) that converts incident radiation 121 into light such as visible light, and a photoelectric conversion element that converts the light converted by the scintillator into a signal charge. The present exemplary embodiment is not limited to such a configuration. A conversion element of direct conversion type that directly converts incident radiation 121 into a signal charge without the provision of a scintillator can be used as the conversion element 2211.

The drive circuit 210 switches on/off the switch elements 2212 via a drive line 222, whereby accumulation in and reading of charges from the conversion elements 2211 are performed. As a result, a radiation image can be obtained. More specifically, the drive circuit 210 applies an ON voltage of a switch element 2212 to a predetermined drive line 222. The switch elements 2212 of respective pixels 221 in the row connected to the predetermined drive line 222 are thereby turned ON, and the charges in the conversion elements 2211 are held by the sample-and-hold circuit 230 via respective signal lines 223. Then, the signal charges held by the sample-and-hold circuit 230 are then sequentially read via the multiplexer 240, amplified by the amplifier 250, and then converted into digital radiation image data by the A/D converter 260. The drive circuit 210 applies an OFF voltage of a switch element 2212 to the predetermined drive line 222, whereby the pixels 221 in the row in which the charge reading has ended return to a charge accumulation state.

The drive circuit 210 thus sequentially drives and scans the pixels 221 in the respective rows of the sensor array 220, and the signal charges of all the pixels 221 are eventually converted into digital values. In such a manner, radiation image data can be read. Such controls on the driving and reading operations of the radiation detection unit 111 are performed by the drive control unit 1121 in the imaging control unit 112 illustrated in FIG. 1.

The imaging control unit 112 performs control to set an operation state of the radiation detection unit 111 and drive the radiation detection unit 111 based on an imaging order and imaging mode information set by the system control apparatus 130 and a connection state of the cable. If the imaging control unit 112 receives an imaging request signal from the irradiation control apparatus 160, the imaging control unit 112 can perform moving image and still image capturing operations in synchronization with the irradiation control apparatus 160. The image processing unit 1122 of the imaging control unit 112 then performs required image processing on radiation image data obtained by an imaging operation. The imaging control unit 112 then performs storage control on the storage unit 113 and transfer control on the irradiation control apparatus 160 that is an external apparatus.

Figure 3:
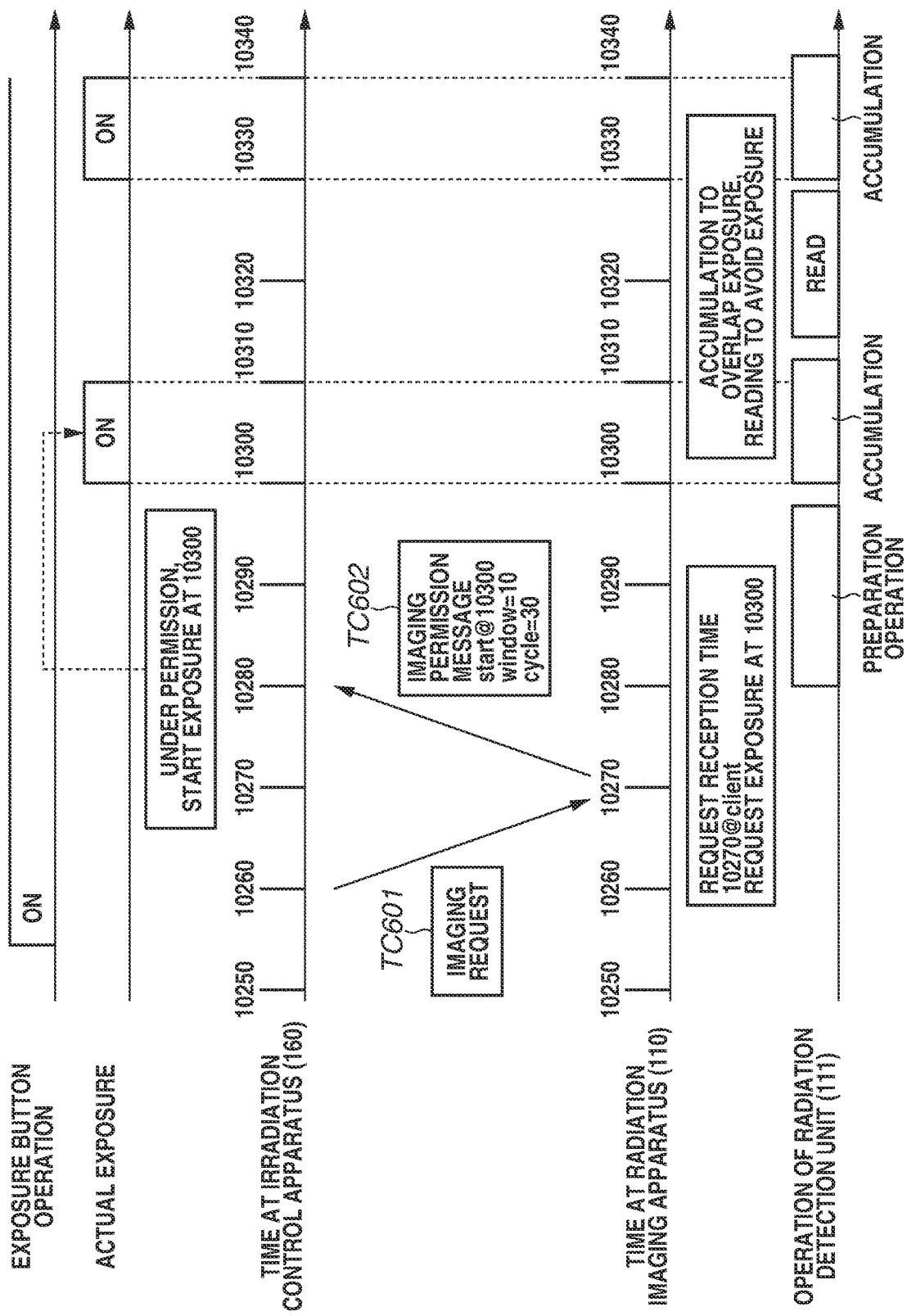
FIG. 3 is a timing chart illustrating a method of synchronization during imaging between a radiation imaging apparatus and an irradiation control apparatus illustrated in FIG. 1 and generation of communication procedure operation timing of a message controlling a start of imaging, according to the first exemplary embodiment.

FIG. 3 is a timing chart illustrating the first exemplary embodiment. FIG. 3 is a timing chart illustrating a method of synchronization during imaging between the radiation imaging apparatus 110 and the irradiation control apparatus 160 illustrated in FIG. 1 and generation of communication procedure operation timing of a message controlling a start of imaging.

In FIG. 3, the clock 1124 included in the radiation imaging apparatus 110 and the clock 163 included in the irradiation control apparatus 160 are previously synchronized with each other. At this time, a difference in time can be corrected by using a time synchronization protocol discussed in the Institute of Electrical and Electronics Engineers (IEEE) 1588 or an original synchronization message.

For example, if an exposure button connected to the radiation control apparatus 170 is pressed, the irradiation control apparatus 160 transmits an imaging request TC601 to the radiation imaging apparatus 110 in the form of a packet message by using wired communication or wireless communication. With respect to a received imaging request time, the radiation imaging apparatus 110 then calculates a scheduled exposure start time from the current state of standby driving. The scheduled exposure start time is suitably set to a time that is sufficient to exchange messages and perform preparation operations of the radiation imaging apparatus 110 and is short enough not to keep the user waiting needlessly with poor operability.

The radiation imaging apparatus 110 then transmits an imaging permission message TC602 including the above-described scheduled exposure start time as a parameter to the irradiation control apparatus 160. In FIG. 3, the imaging permission message TC602 also includes information corresponding to the length of a radiation pulse and a frame rate. However, such information does not necessarily need to be included in the imaging permission message TC602, and can be set prior to imaging by some other means. Conversely, parameters not explicitly specified here can be included in and transmitted with the imaging permission message TC602.

The irradiation control apparatus 160 then receives the imaging permission message TC602. If the time measured by the internal clock 163 reaches the scheduled exposure start time, the irradiation control apparatus 160 starts generating radiation irradiation timing pulses. A moving image can be captured by repeating exposure based on the specified length of the radiation pulse and the frame rate information.

Meanwhile, the radiation imaging apparatus 110 is performing a standby operation. If the time measured by the internal clock 1124 reaches the scheduled exposure start time, the radiation imaging apparatus 110 controls the operation of the radiation detection unit 111 to an accumulation state in preparation for irradiation with the radiation 121. After a lapse of time as much as the length of a radiation pulse from that time, i.e., after the time indicated by the clock 1124 reaches "10310" in FIG. 3, the radiation imaging apparatus 110 switches the operation of the radiation detection unit 111 to a read operation and obtains radiation image data. Like the irradiation control apparatus 160, the radiation imaging apparatus 110 (e.g., the imaging control unit 112) then performs accumulation operations and read operations based on the time of the clock 1124 to achieve the predetermined frame rate.

As described above, the synchronization control between the read operation and the radiation irradiation is performed based on the times synchronized in advance. Accordingly, irradiation timing in each frame does not need to be synchronized by using a message on a packet network. Moving image capturing can thus be performed at stable timing without being affected by a message delay or disappearance. While an example of moving image capturing control using time synchronization in a packet network has been described, this is not restrictive. If the effect of a message delay or disappearance between the radiation imaging apparatus 110 and the irradiation control apparatus 160 is allowable, the radiation imaging apparatus 110 can notify the irradiation control apparatus 160 of a radiation irradiation request message, for example, at timing when the radiation detection unit 111 enters the accumulation state in each frame. Alternatively, the irradiation control apparatus 160 can take the initiative and transmit a synchronization message at timing when the radiation pulse ends so that the radiation imaging apparatus 110 performs image reading. The communication is not limited to that over a packet network such as an Ethernet network and a wireless LAN, and a dedicated synchronization signal line can be used to synchronize the moving image capturing operations.

Figure 4:
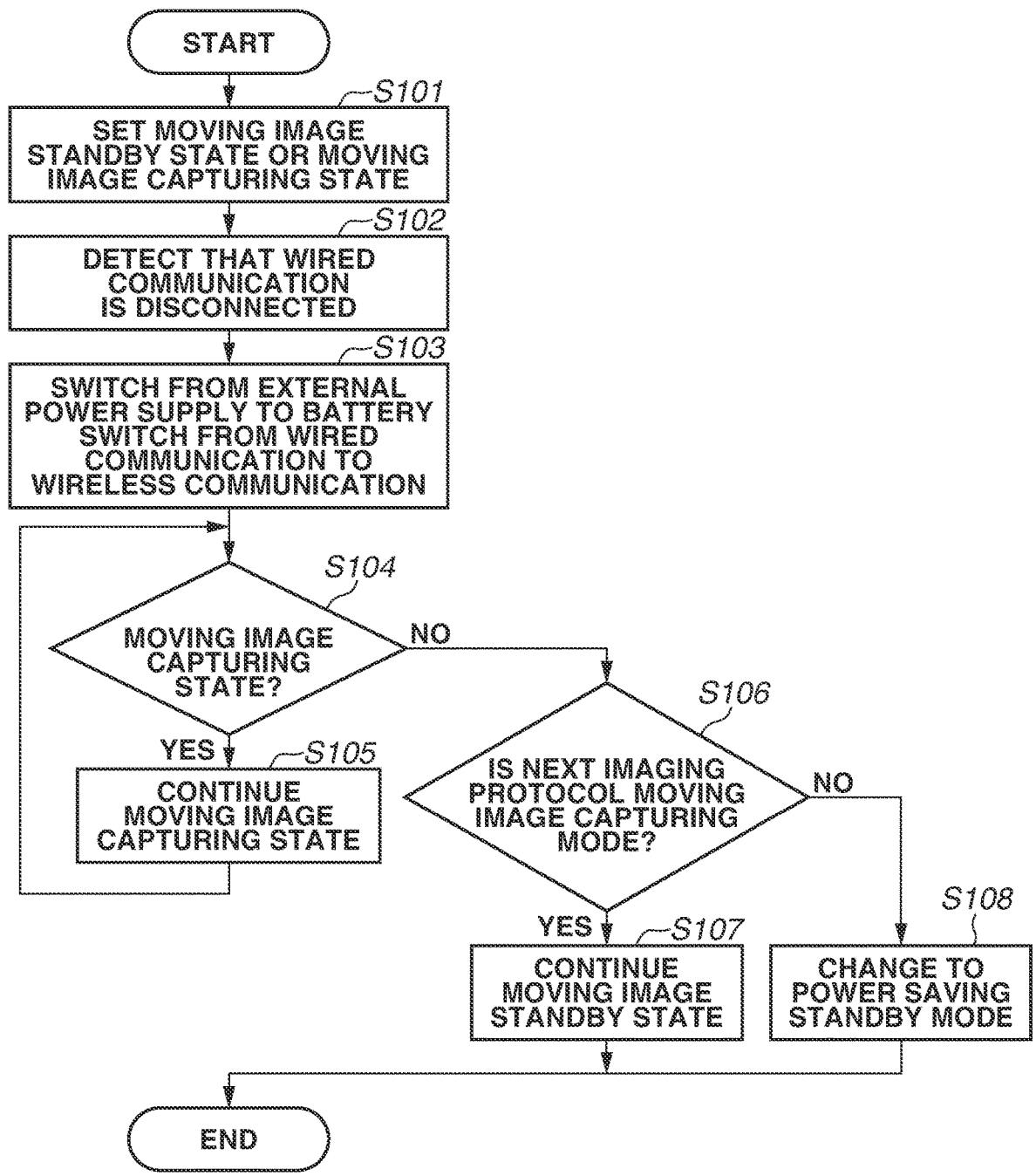
FIG. 4 is a flowchart illustrating an example of a processing procedure of a control method of the radiation imaging apparatus according to the first exemplary embodiment performed in a case where wired communication with the irradiation control apparatus is disconnected.

FIG. 4 is a flowchart illustrating an example of a processing procedure of a control method of the radiation imaging apparatus 110 according to the first exemplary embodiment performed in a case where wired communication with the irradiation control apparatus 160 is disconnected.

If the radiation imaging apparatus 110 is connected to the irradiation control apparatus 160 in a wired manner (by a cable) via the connection terminal 190, the radiation imaging apparatus 110 operates on power supplied from the power supply 162 of the irradiation control apparatus 160 and performs control by Ethernet-based wired communication, for example. In such a state, the radiation imaging apparatus 110 can capture a moving image at high frame rate. The radiation imaging apparatus 110 can be kept operating in a moving image standby state, which is a standby state for moving image capturing, so that high-speed moving image capturing can be performed basically any time. In the present exemplary embodiment, for example, the moving image standby state is such that image reading is regularly performed with the same power consumption as in a moving image capturing state in which a moving image is captured and at the same frame rate as in the moving image capturing state (i.e., the time to obtain each frame constituting the moving image is the same as in the moving image capturing state). In the present exemplary embodiment, the generation of the radiation 121 from the radiation generation apparatus 120 is stopped in the moving image standby state.

Without a moving image capturing request, the image reading here is only performed to sweep out dark charges accumulated in the radiation detection unit 111, and the read image data can be simply discarded. In the moving image standby state, the reading and discarding of the image data with the same power consumption and at the same frame rate as in the moving image capturing state reduces variations in dark charges and enables smooth transition to stable moving image capturing when a moving image capturing request is given. Alternatively, the image read in the moving image standby state can be stored in the storage unit 113 as an offset image. By using the offset image, a radiation image obtained under irradiation with the radiation 121 during actual moving image capturing can be corrected to obtain a captured image in which dark charge components are corrected. An offset correction with even reduced noise components can be performed by using an average image of images obtained from a plurality of frames without radiation irradiation as the offset image. In the moving image standby state, the operation of generating an offset image from the read image can be repeated.

In the flowchart illustrated in FIG. 4, in step S101, the imaging control unit 112 performs control to set the above-described moving image standby state or moving image capturing state.

In step S102, the connection terminal 190 is detached from the radiation imaging apparatus 110, and the imaging control unit 112 detects that the wired communication is disconnected.

In step S103, the imaging control unit 112 performs processing for switching the method of power supply of the radiation imaging apparatus 110 via the power supply control unit 116 from the external power supply using the power supply 162 of the irradiation control apparatus 160 to power supply using the battery 117 of the radiation imaging apparatus 110. In addition, the imaging control unit 112 immediately performs processing for switching the communication with the irradiation control apparatus 160 to wireless communication since the wired communication is disconnected.

Performing the processing of step S103 results in the power supply using the battery 117 and a wireless communication operation. High-speed moving image capturing that can be performed during wired communication becomes difficult. Thus, in normal conditions, the radiation imaging apparatus 110 can transition to a power saving standby state, which is a standby state with lower power consumption, to suppress the consumption of the battery 117. However, if the disconnection of the wired communication is a temporary one or an unintentional one, the transition to the power saving standby state can possibly raise issues in resuming moving image capturing afterward. Examples of the issues include that moving image capturing is unable to be immediately performed, and that the moving image needs to be captured again from the beginning. Then, in the present exemplary embodiment, the processing of steps S104 to S108 of FIG. 4 to be described below is performed to suppress the occurrence of the issues so that the subsequent moving image capturing can be appropriately performed.

Specifically, in step S104, the imaging control unit 112 determines whether the operation state when the wired communication is disconnected in step S102 is the moving image capturing state.

If, as a result of the determination in step S104, the operation state when the wired communication is disconnected in step S102 is the moving image capturing state (YES in step S104), the processing proceeds to step S105.

In step S105, the imaging control unit 112 determines that the disconnection of the wired communication in step S102 is an unintentional one, and continues setting the moving image capturing state as the operation state of the radiation imaging apparatus 110. The processing then returns to step S104, and the imaging control unit 112 determines, for example, whether the moving image capturing state is maintained.

On the other hand, if, as a result of the determination in step S104, the operation state when the wired communication is disconnected in step S102 is not the moving image capturing state (i.e., is the moving image standby state) (NO in step S104), the processing proceeds to step S106.

In step S106, the imaging control unit 112 determines whether a next imaging protocol is already set by the system control apparatus 130 and the next imaging protocol is a moving image capturing mode.

If, as a result of the determination in step S106, a next imaging protocol is already set by the system control apparatus 130 and the next imaging protocol is the moving image capturing mode (YES in step S106), the processing proceeds to step S107.

In step S107, the imaging control unit 112 determines that the disconnection of the wired communication in step S102 is a temporary one, and continues setting the moving image standby state as the operation state of the radiation imaging apparatus 110.

On the other hand, if, as a result of the determination in step S106, there is no next imaging protocol set by the system control apparatus 130 or the next imaging protocol is not the moving image capturing mode (NO in step S106), the processing proceeds to step S108. Examples of the case where the next imaging protocol is not the moving image capturing mode include when a still image capturing mode for capturing a still image is set and when an imaging mode with a low frame rate capable of transfer even by using wireless communication is set.

In step S108, the imaging control unit 112 changes the operation state of the radiation imaging apparatus 110 to the power saving standby state, which is a standby state with power consumption lower than in the moving image capturing state, to suppress the consumption of the battery 117. In the power saving standby state, the power consumption can be made lower than in the moving image capturing state, for example, by using a power setting lower than that in the high-frame rate moving image capturing state or by making the read cycles of dark charges longer than in the moving image capturing state.

If the processing of step S107 ends or the processing of step S108 ends, the processing of the flowchart illustrated in FIG. 4 ends.

Now, suppose that the power saving standby state is set in step S108 and then the operation state transitions to the moving image capturing state. In such a case, the state of power consumption needs to return to the setting of the moving image capturing state, and the frame rate of the reading operation needs to be changed to that in the moving image capturing state. This increases susceptibility to variations in dark charges, and needs a preparation time to obtain captured images of stable image quality. However, as far as still image capturing and low-frame rate moving image capturing are concerned, the radiation imaging apparatus 110 can obtain images while suppressing the effect of variations in dark charges. For example, the radiation imaging apparatus 110 can obtain such images by obtaining an offset image without irradiation with the radiation 121 immediately after a radiation image is obtained under the irradiation with the radiation 121, and performing an offset correction using the offset image obtained immediately afterward. Such a method is difficult to apply to a high-frame rate moving image since two or more accumulation operations and read operations are needed in obtaining a single frame of captured image.

By performing the processing illustrated in FIG. 4, the moving image capturing state or the moving image standby state can be continued if the wired communication is disconnected and the disconnection of the wired communication is considered to be a temporary one or an unintentional one. Even if the moving image capturing state or the moving image standby state is continued after the disconnection of the wired communication, the remaining level of the battery 117 can fall to or below a certain level or the surface temperature of the radiation imaging apparatus 110 can become too high. In such cases, the power saving standby state can be set instead in terms of the consumption of the battery 117 or from a safety point of view.

Figure 5:
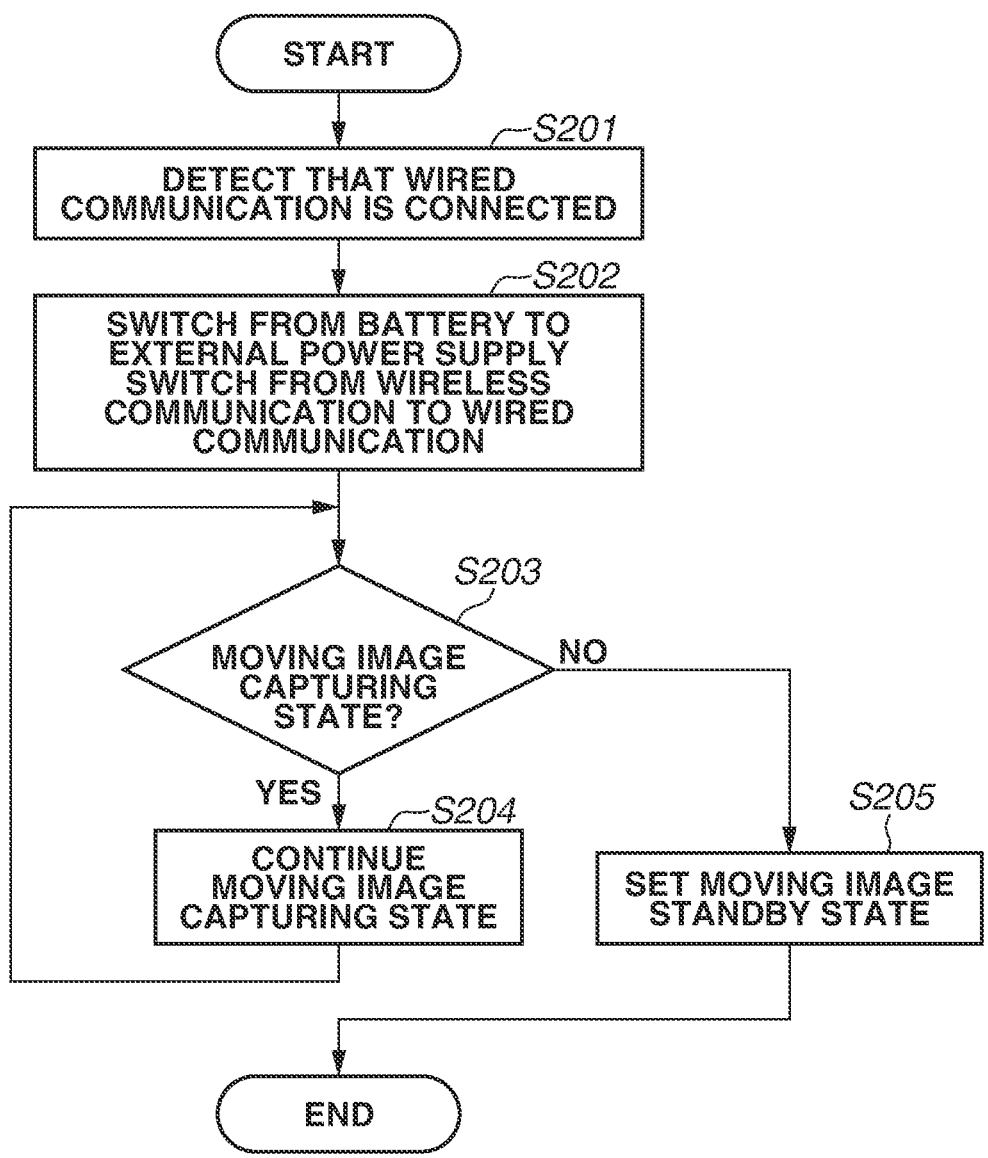
FIG. 5 is a flowchart illustrating an example of a processing procedure of a control method performed in a case where the radiation imaging apparatus according to the first exemplary embodiment transitions from the state in which the wired communication with the irradiation control apparatus is disconnected to a state where the wired communication is connected.

FIG. 5 is a flowchart illustrating an example of a processing procedure of a control method performed in a case where the radiation imaging apparatus 110 according to the first exemplary embodiment transitions from the state in which the wired communication with the irradiation control apparatus 160 is disconnected to a state in which the wired communication is connected.

In step S201, the connection terminal 190 is connected to the radiation imaging apparatus 110, and the imaging control unit 112 detects that the wired communication is connected.

In step S202, the imaging control unit 112 performs processing for switching the power supply method of the radiation imaging apparatus 110 via the power supply control unit 116 from the power supply using the battery 117 of the radiation imaging apparatus 110 to the external power supply using the power supply 162 of the irradiation control apparatus 160 through wired communication. Since the wired communication is connected, the imaging control unit 112 also performs processing for switching the communication with the irradiation control apparatus 160 from wireless communication to Ethernet-based wired communication.

In step S203, the imaging control unit 112 determines whether the operation state before the connection of the wired communication in step S201 is the moving image capturing state.

If, as a result of the determination in step S203, the operation state before the connection of the wired communication in step S201 is the moving image capturing state (YES in step S203), the processing proceeds to step S204. An example of the case where the processing proceeds to step S204 is when the state in which the moving image capturing state is continued due to an unintentional disconnection of the wired communication as in step S105 of FIG. 4 returns to the state in which the wired communication is connected by re-insertion of the cable.

In step S204, the imaging control unit 112 continues the setting of the moving image capturing state as the operation state of the radiation imaging apparatus 110. The processing then returns to step S203, and the imaging control unit 112 determines, for example, whether the moving image capturing state is maintained.

On the other hand, if, as a result of the determination in step S203, the operation state before the connection of the wired communication in step S201 is not the moving image capturing state (NO in step S203), the processing proceeds to step S205.

In step S205, the imaging control unit 112 sets the moving image standby state as the operation state of the radiation imaging apparatus 110. In this case, by setting the moving image standby state instead of the power saving standby state, the radiation imaging apparatus 110 can immediately perform high-frame rate moving image capturing afterward when the moving image capturing needs to be performed. If the processing of step S205 ends, the processing of the flowchart illustrated in FIG. 5 ends.

Figure 6:
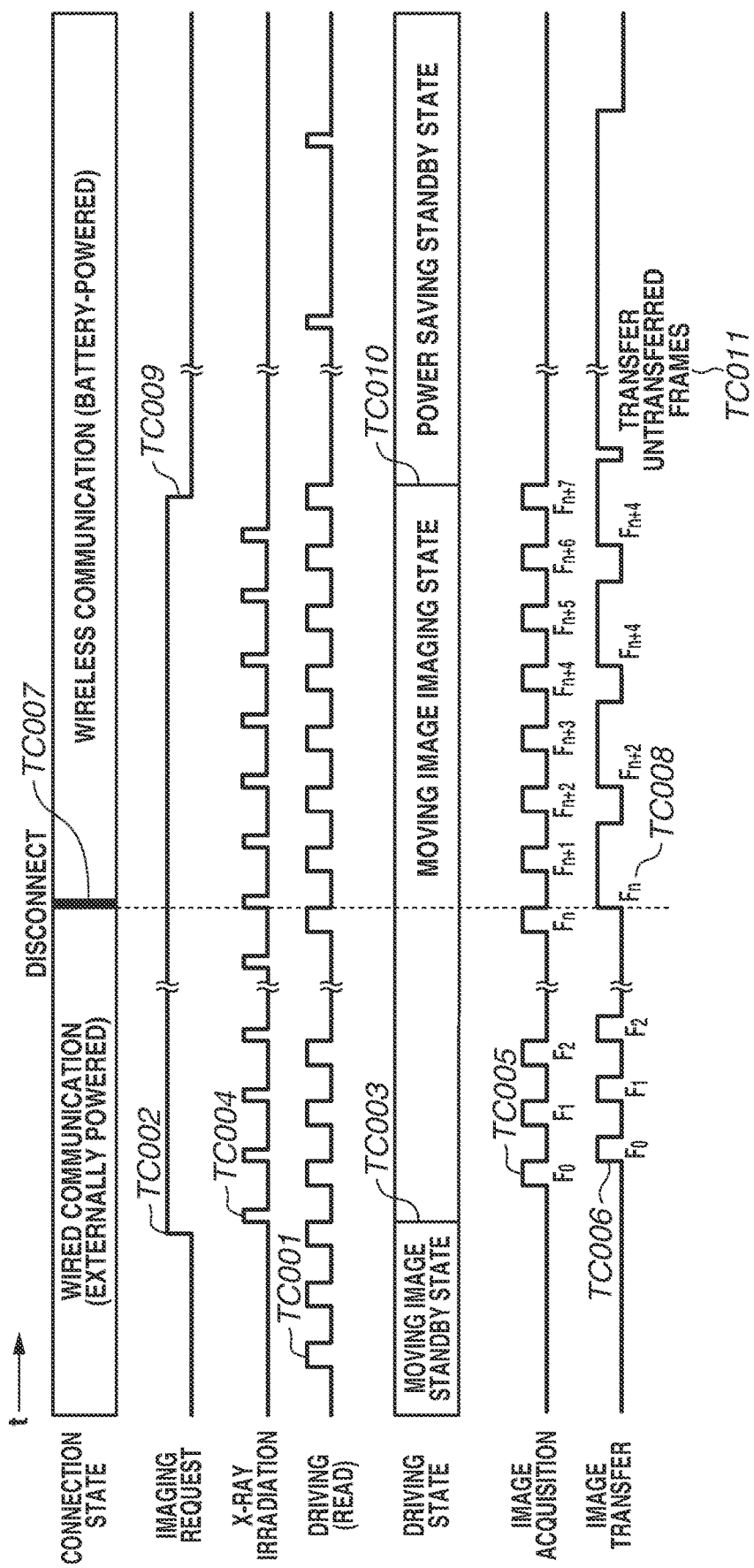
FIG. 6 is a timing chart illustrating an example of a processing procedure of a control method performed in a case where the wired communication with the irradiation control apparatus is disconnected when the radiation imaging apparatus according to the first exemplary embodiment is in an moving image capturing state.

FIG. 6 is a timing chart illustrating an example of a processing procedure of a control method performed in a case where the wired communication with the irradiation control apparatus 160 is disconnected when the radiation imaging apparatus 110 according to the first exemplary embodiment is in the moving image capturing state. In other words, FIG. 6 is a timing chart corresponding to the processing of the flowchart illustrated in FIG. 4 according to the first exemplary embodiment. In the description of FIG. 6, the processing of the radiation imaging apparatus 110 can be performed, for example, with the imaging control unit 112 of the radiation imaging apparatus 110 as a main component.

In FIG. 6, a connection state represents a communication connection state of the radiation imaging apparatus 110 with the irradiation control apparatus 160. An imaging request represents a request for moving image capturing. In FIG. 6, X-ray irradiation represents the irradiation of the object H with X-rays generated by the radiation generation apparatus 120 in a case where X-rays are applied as the radiation 121. In FIG. 6, driving (read) represents read timing of the radiation detection unit 111. A driving state represents the operation state of the radiation imaging apparatus 110 set by the imaging control unit 112. In FIG. 6, image acquisition represents acquisition timing of each frame (each frame image) constituting the moving image that the imaging control unit 112 obtains from the radiation detection unit 111. In FIG. 6, image transfer represents the timing of transfer of each frame obtained from the radiation detection unit 111 to the irradiation control apparatus 160.

Suppose initially that the radiation imaging apparatus 110 is operating in the moving image standby state when performing wired communication with the irradiation control apparatus 160. In the moving image standby state, for example, at TC001, the radiation imaging apparatus 110 alternately performs a read operation and an accumulation operation on the radiation detection unit 111 on a regular basis to sweep out dark charges. Since the radiation imaging apparatus 110 is in a standby operation, the radiation imaging apparatus 110 is not irradiated with X-rays from the radiation generation apparatus 120 and does not transfer a read image to the system control apparatus 130. For example, the radiation imaging apparatus 110 performs read operations and accumulation operations at the same cycles as the previously-set cycles in the moving image capturing mode, whereby variations in accumulation time after a transition to the moving image capturing state can be suppressed.

Next, the user presses the exposure button, and an imaging request turns ON at TC002. The radiation imaging apparatus 110 is notified of the information via the irradiation control apparatus 160.

The radiation imaging apparatus 110 receiving the imaging request enters the moving image capturing state at TC003, and performs control so that X-ray irradiation at TC004 is performed in synchronization with the next accumulation operation.

Next, the radiation imaging apparatus 110 stores each frame of the moving image captured by read operations after the X-ray irradiation at TC004 into the storage unit 113 of the radiation imaging apparatus 110 at TC005. The radiation imaging apparatus 110 then performs imaging processing such as offset correction and defect correction, and then performs image transfer to the irradiation control apparatus 160 at TC006. The radiation imaging apparatus 110 performs a moving image capturing operation by repeating the X-ray irradiation, reading, and transfer operations.

Next, processing performed when the disconnection of the wired communication is detected in the moving image capturing state will be described. The radiation imaging apparatus 110 detects the disconnection of the wired communication with the irradiation control apparatus 160 at TC007. The radiation imaging apparatus 110 determines that the disconnection occurring in the moving image capturing state is an unintentional one, and performs control to continue the setting of the moving image capturing mode. At this time, the radiation imaging apparatus 110 switches from the external power supply to the power supply by the battery 117, and switches from the wired communication to wireless communication. At this time, the radiation imaging apparatus 110 maintains the read and accumulation operations of the radiation detection unit 111 at the same cycles as before the disconnection of the wired communication, and also maintains the X-ray irradiation control in synchronization with the accumulation operations. Wireless communication typically has communication speed lower than that of wired communication, and image transfer at the frame rate of the moving image capturing state becomes difficult. In such a case, image transfer is performed, for example, at reduced frame rate capable of transferring by using wireless communication.

For example, suppose that an image acquisition frame $F_n$ illustrated in FIG. 6 is being transferred. At the time of the next image acquisition frame $F_{n+1}$, the transfer of the image acquisition frame $F_n$ is not completed yet. In such a case, the image of the image acquisition frame $F_{n+1}$ not transferred at this time is stored in the storage unit 113 of the radiation imaging apparatus 110. Similarly, the image of an image acquisition frame $F_{n+3}$ is unable to be transferred during transfer of an image acquisition frame $F_{n+2}$. The image of the image acquisition frame $F_{n+3}$ is stored in the storage unit 113. In such a manner, the images of frames unable to be transferred on time by using the wireless communication are stored in the storage unit 113, whereby the moving image capturing state at the same frame rate as before the disconnection of the wired communication is maintained.

Suppose that the moving image capturing request is turned off in such a state, and the radiation imaging apparatus 110 detects the end of imaging at TC009. If the next setting of the imaging protocol is not scheduled, the radiation imaging apparatus 110 changes its operation state to the power saving standby state at TC010 to suppress the consumption of the battery 117. Then, the radiation imaging apparatus 110 transfers the images of the untransferred frames that have been unable to be transferred and been stored in the storage unit 113 to the irradiation control apparatus 160 after the end of the moving image capturing state. In the power saving standby state, the power consumption can be reduced, for example, by making the read cycles of dark charges from the radiation detection unit 111 longer than in the moving image capturing state. As illustrated in FIG. 6, to immediately switch from the wired communication to the wireless communication, the radiation imaging apparatus 110 can desirably be prepared in a state capable of wireless communication in advance even when the cable is connected.

Figure 7:
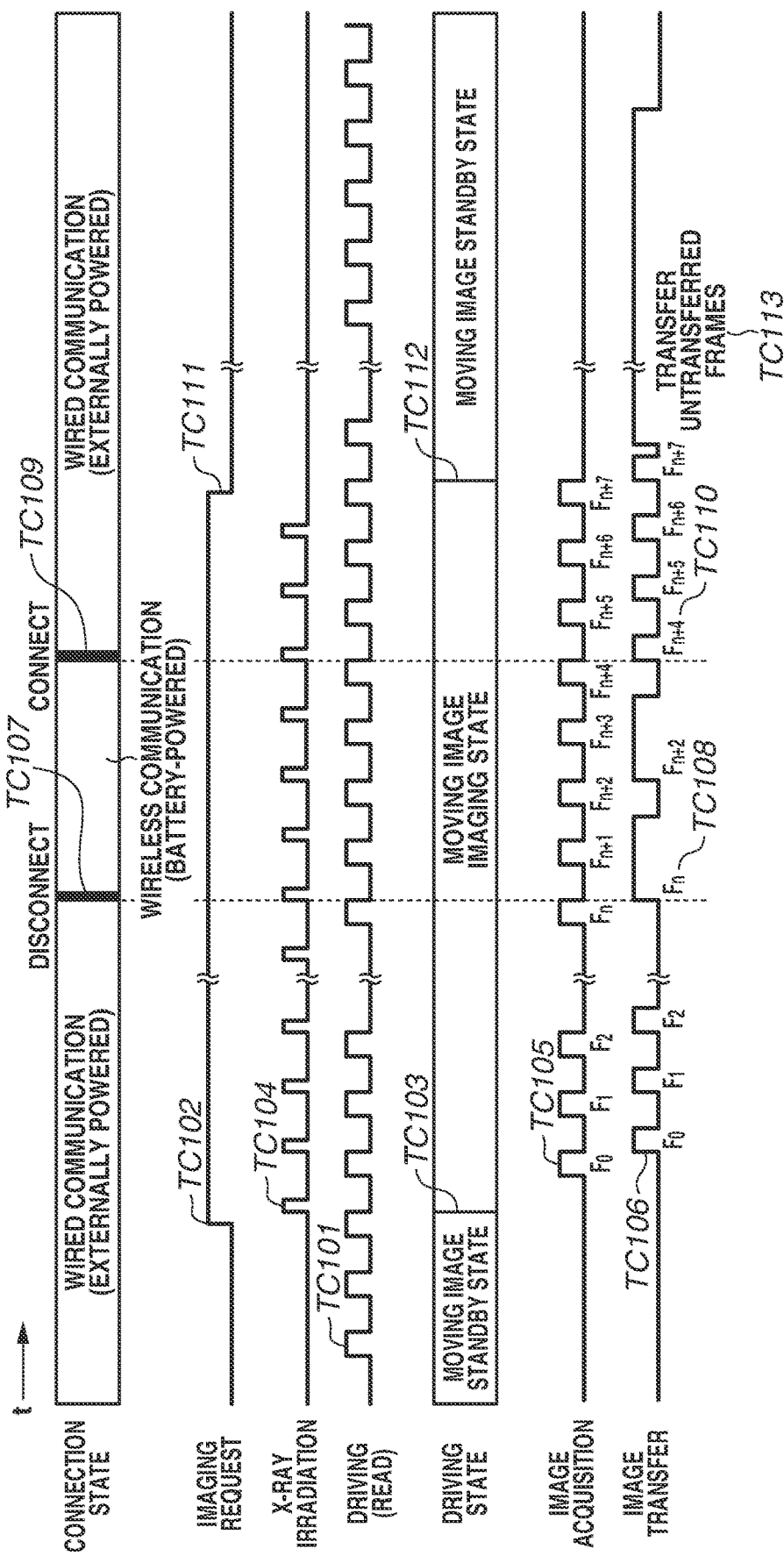
FIG. 7 is a timing chart illustrating an example of a processing procedure of a control method performed in a case where the radiation imaging apparatus according to the first exemplary embodiment transitions from the state in which the wired communication with the irradiation control apparatus is disconnected to a state in which the wired communication is connected again.

FIG. 7 is a timing chart illustrating an example of a processing procedure of a control method performed in a case where the radiation imaging apparatus 110 according to the first exemplary embodiment transitions from the state in which the wired communication with the irradiation control apparatus 160 is disconnected to a state in which the wired communication is connected again. In other words, FIG. 7 is a timing chart corresponding to the processing of the flowchart illustrated in FIG. 5. In FIG. 7, a description similar to that of FIG. 6 will be omitted. In the description of FIG. 7, the processing of the radiation imaging apparatus 110 can be performed, for example, with the imaging control unit 112 of the radiation imaging apparatus 110 as a main component.

In FIG. 7, the operations up to the detection of the disconnection of the wired communication in the moving image capturing state at TC107 and the image transfer by using wireless communication at TC108 are similar to those up to TC007 and TC008 in FIG. 6.

If the radiation imaging apparatus 110 in such a state detects the reconnection of the wired communication at TC109, the radiation imaging apparatus 110 switches its power supply method from the power supply using the battery 117 to the external power supply, and switches from the wireless communication to the wired communication. At that time, the radiation imaging apparatus 110 continues the moving image capturing state, and maintains the read and accumulation operations of the radiation detection unit 111 at the same cycles regardless of the connection of the wired communication.

Switching to the wired communication enables the radiation imaging apparatus 110 to transfer images at the frame rate of the moving image capturing at TC110. In the subsequent transfer operations, image transfer can be performed each time an image is read. In FIG. 7, the wired communication is illustrated to be immediately available after the wireless communication. In fact, Ethernet link processing can take some time between when the cable is connected and when the wired communication becomes available. In such a case, the operation using the wireless communication can desirably be continued until the wired communication becomes available.

Suppose that after the wired connection, the moving image capturing request is turned OFF, and the radiation imaging apparatus 110 detects the end of imaging at TC111. The radiation imaging apparatus 110 enters the moving image standby state, and makes preparations at TC112 for the next moving image capturing. At TC113, the radiation imaging apparatus 110 transfers the images of the untransferred frames failed to be transferred while the communication is switched to the wireless communication.

In the radiation imaging apparatus 110 according to the first exemplary embodiment, the imaging control unit 112 performs control to set the moving image capturing state (step S105) in a first case where the wired communication is disconnected and the operation state is the moving image capturing state in which a moving image is captured (YES in step S104 of FIG. 4). In a second case where the wired communication is disconnected, the operation state is not the moving image capturing state, and the moving image capturing mode is set as the next imaging protocol (YES in step S106 of FIG. 4), the imaging control unit 112 performs control to set the moving image standby state that is the standby state for moving image capturing (step S107). If the moving image standby state is set, the imaging control unit 112 stops the generation of the radiation 121 from the radiation generation apparatus 120, and performs control to make the power consumption the same as in the moving image capturing state and make the time for the radiation detection unit 111 to obtain each frame of the moving image the same as in the moving image capturing state.

According to such a configuration, if the wired communication of the radiation imaging apparatus 110 with the irradiation control apparatus 160 that is an external apparatus is temporarily or unintentionally disconnected, the subsequent moving image capturing can be appropriately performed. For example, the preparation time to enable stable moving image capturing can be reduced, and the subsequent moving image capturing can therefore be appropriately performed. For example, even in a case of imaging that needs a series of a predetermined number of consecutive pieces of image data like tomosynthesis, the imaging is not interrupted. Since ineffective irradiation with the radiation 121 can be avoided, the subsequent moving image capturing can be appropriately performed. In the present exemplary embodiment, the moving image capturing operation is continued by storing the images of the frames unable to be transferred while the communication is switched to the wireless communication into the storage unit 113. The storage unit 113 therefore desirably has a storage capacity enough for storing images as many as the number of frames required for series radiography such as tomosynthesis.

Next, a second exemplary embodiment will be described. In the following description of a second exemplary embodiment, components similar to those in the above-described first exemplary embodiment are not described. Differences from the first exemplary embodiment will be described below.

A radiation imaging system according to the second exemplary embodiment has a schematic configuration similar to that of the radiation imaging system 100 according to the first exemplary embodiment illustrated in FIG. 1. A method for controlling a radiation imaging apparatus 110 according to the second exemplary embodiment is also similar to that according to the above-described first exemplary embodiment illustrated in FIGS. 4 and 5.

Different from the radiation imaging apparatus 110 according to the above-described first exemplary embodiment, the radiation imaging apparatus 110 according to the second exemplary embodiment is an apparatus not including the storage unit 113 for storing images as many as the number of frames required for series radiography.

Figure 8:
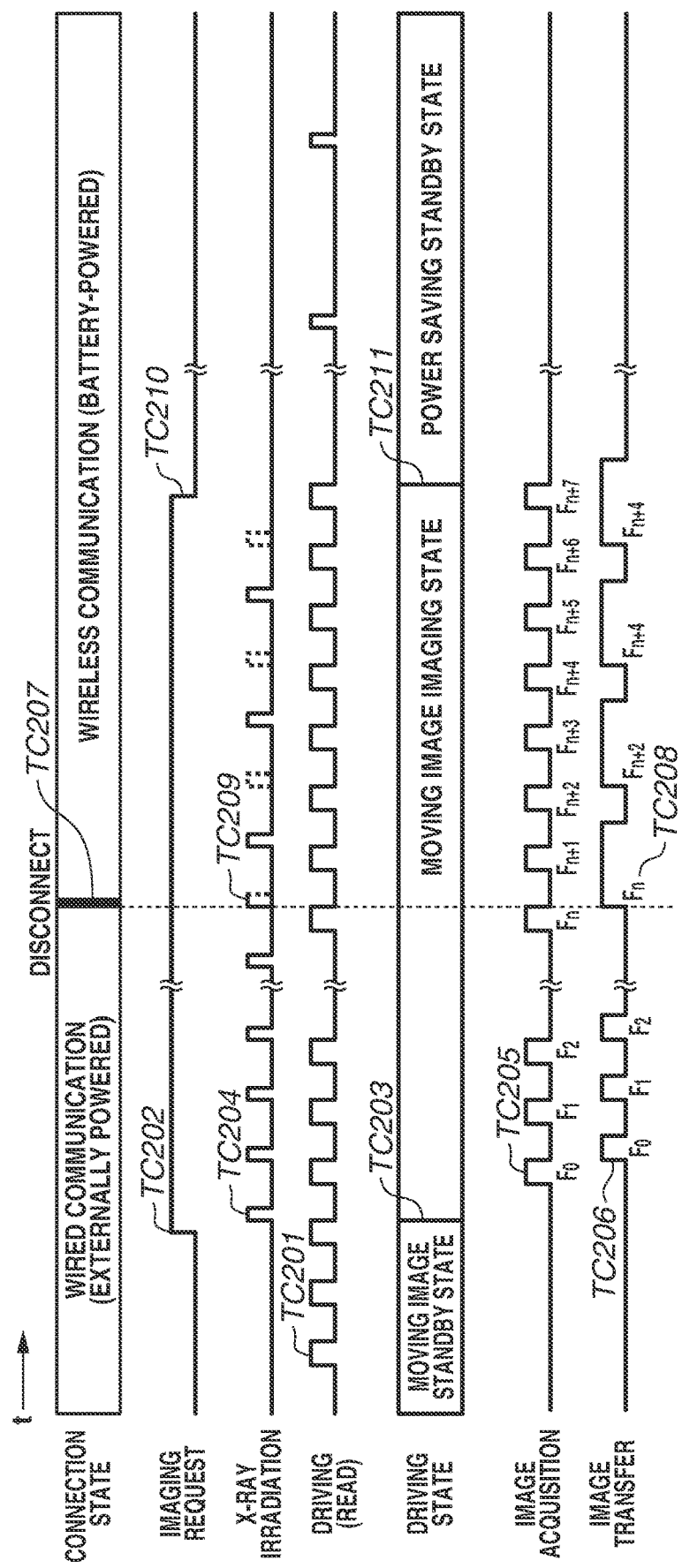
FIG. 8 is a timing chart illustrating an example of a processing procedure of a control method performed in a case where wireless communication with an irradiation control apparatus is disconnected when a radiation imaging apparatus according to a second exemplary embodiment is in a moving image capturing state.

FIG. 8 is a timing chart illustrating an example of a processing procedure of a control method performed in a case where the wired communication with the irradiation control apparatus 160 is disconnected when the radiation imaging apparatus 110 according to the second exemplary embodiment is in the moving image capturing state. In other words, FIG. 8 is a timing chart corresponding to the processing of the flowchart illustrated in FIG. 4 according to the second exemplary embodiment.

In FIG. 8, the operations up to the detection of the disconnection of the wired communication in the moving image capturing state at TC207 and the image transfer by using wireless communication at TC208 are similar to those up to TC007 and TC008 in FIG. 6.

At the time of the image acquisition frame $F_{n+1}$ illustrated in FIG. 8, the transfer of the image acquisition frame $F_n$ is not completed. In the present exemplary embodiment, as described above, the storage unit 113 does not have a capacity sufficient to store frames unable to be transferred. If X-ray irradiation is performed at the timing of TC209, the X-ray irradiation ends up being ineffective since the image of the image acquisition frame $F_{n+1}$ is unable to be transferred. The radiation imaging apparatus 110 (e.g., imaging control unit 112) according to the present exemplary embodiment then performs control not to perform X-ray irradiation for a not-transferable frame at the timing of TC209. As illustrated in FIG. 8, the read and accumulation operations of the radiation detection unit 111 are continued at the same cycles as before the disconnection of the wired communication. However, needless X-ray irradiation can be suppressed by performing control not to perform X-ray irradiation during an accumulation operation at a timing when the read image is unable to be transferred. This lowers the image transfer rate, whereas variations of charge accumulation can be suppressed and moving image capturing can be continued without a change in image quality by continuing the read and accumulation operations at the same cycles as when the wired communication is connected.

When the cable is reconnected thereafter, the moving image capturing can be continued with the same stable image quality since the cycles of the read and accumulation operations of the radiation detection unit 111 remain unchanged. Suppose that the moving image capturing request is turned OFF in such a state, and the radiation imaging apparatus 110 (e.g., imaging control unit 112) according to the present exemplary embodiment detects the end of imaging at TC210. If the next setting of the imaging protocol is not scheduled, the radiation imaging apparatus 110 changes its operation state to the power saving standby state at TC211 to suppress the consumption of the battery 117.

As described above, even if the storage unit 113 does not have a capacity sufficient to store frames unable to be transferred, the radiation imaging apparatus 110 according to the second exemplary embodiment can appropriately perform the subsequent moving image capturing when the wired communication is temporarily or unintentionally disconnected. Such a configuration is also applicable to a moving image capturing state in which images do not need to be stored like fluoroscopy, for example. According to the second exemplary embodiment, the generation of the radiation 121 from the radiation generation apparatus 120 is controlled to be stopped to obtain frames unable to be transferred on time. Needless radiation irradiation of the object H can thus be suppressed.

Next, a third exemplary embodiment will be described. In the following description of the third exemplary embodiment, components similar to those of the above-described first and second exemplary embodiments are not described. Differences from the above-described first and second exemplary embodiments will be described.

A radiation imaging system according to the third exemplary embodiment has a schematic configuration similar to that of the radiation imaging system 100 according to the first exemplary embodiment illustrated in FIG. 1.

Similar to the radiation imaging apparatus 110 according to the above-described second exemplary embodiment, a radiation imaging apparatus 110 according to the third exemplary embodiment is an apparatus not including the storage unit 113 for storing images as many as the number of frames required for series radiography. The radiation imaging apparatus 110 needs some time to switch to wireless communication when wired communication is disconnected. For example, suppose that in the third exemplary embodiment, wireless communication is fully cut off during wired communication. If the wired communication is disconnected, the radiation imaging apparatus 110 establishes wireless communication and switches the communication operation.

Figure 9:
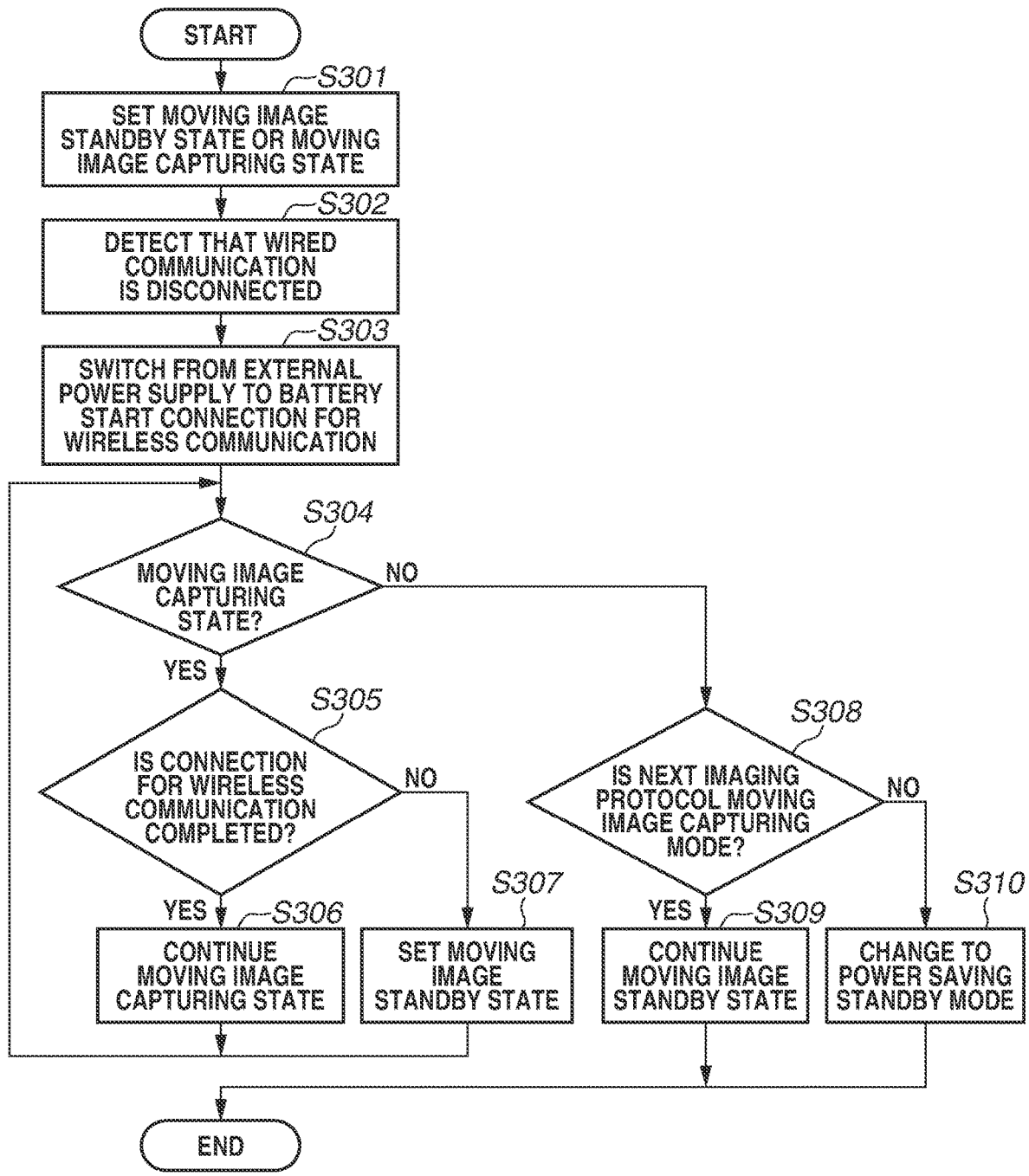
FIG. 9 is a flowchart illustrating an example of a processing procedure of a control method of a radiation imaging apparatus according to a third exemplary embodiment of the performed in a case where wired communication with an irradiation control apparatus is disconnected.

FIG. 9 is a flowchart illustrating an example of a processing procedure of a control method of the radiation imaging apparatus 110 according to the third exemplary embodiment performed in a case where the wired communication with the irradiation control apparatus 160 is disconnected.

In step S301, like in step S101 of FIG. 4, the imaging control unit 112 performs control to set the moving image standby state or the moving image capturing state.

In step S302, like in step S102 of FIG. 4, the imaging control unit 112 detects that the wired communication is disconnected.

In step S303, the imaging control unit 112 performs processing for switching the power supply method of the radiation imaging apparatus 110 via the power supply control unit 116 from the external power supply using the power supply 162 of the irradiation control apparatus 160 to the power supply using the battery 117 of the radiation imaging apparatus 110. In addition, the imaging control unit 112 starts a connection through wireless communication (wireless connection) since the wired communication is disconnected.

In step S304, the imaging control unit 112 determines whether the operation state when the wired communication is disconnected in step S302 is the moving image capturing state.

If, as a result of the determination in step S304, the operation state when the wired communication is disconnected in step S302 is the moving image capturing state (YES in step S304), the processing proceeds to step S305. In the case where the processing proceeds to step S305, the disconnection of the wired communication in step S302 is determined to be an unintentional one.

In step S305, the imaging control unit 112 determines whether the connection (establishment) of the wireless communication is completed and wireless communication is available.

If, as a result of the determination in step S305, the connection (establishment) of the wireless communication is completed and wireless communication is available (YES in step S305), the processing proceeds to step S306.

In step S306, the imaging control unit 112 continues the setting of the moving image capturing state as the operation state of the radiation imaging apparatus 110. Then, the processing returns to step S304, and the imaging control unit 112 determines, for example, whether the moving image capturing state is maintained.

On the other hand, if, as a result of the determination in step S305, the connection (establishment) of the wireless communication is not completed and wireless communication is not available (NO in step S305), the processing proceeds to step S307.

In step S307, the imaging control unit 112 sets the moving image standby state as the operation state of the radiation imaging apparatus 110. The reason is that the communication method is currently being switched to the wireless communication, and ineffective radiation irradiation can possibly be made on the object H if the moving image capturing is simply continued. Then, the processing returns to step S304, and the imaging control unit 112 determines, for example, whether the moving image capturing mode is maintained. If the moving image capturing mode is maintained, the imaging control unit 112 continues the setting of the moving image standby state until the wireless communication becomes available. Then, if the wireless communication becomes available (YES in step S305), the imaging control unit 112 sets the moving image capturing state as the operation state of the radiation imaging apparatus 110. In such a manner, the imaging control unit 112 sets the moving image standby state in which the radiation irradiation of the object H is suspended and the cycles of the read and accumulation operations of the radiation detection unit 111 are maintained the same as in the moving image capturing state until the wireless communication is confirmed to be available after the disconnection of the wired communication. This enables moving image capturing with stable image quality without being affected by variations of charge accumulation when the operation state transitions to the moving image capturing state afterward.

On the other hand, if, as a result of the determination in step S304, the operation state when the wired communication is disconnected in step S302 is not the moving image capturing state (i.e., the moving image standby state) (NO in step S304), the processing proceeds to step S308.

In step S308, similar in step S106 of FIG. 4, the imaging control unit 112 determines whether a next imaging protocol is already set by the system control apparatus 130 and the next imaging protocol is the moving image capturing mode.

If, as a result of the determination in step S308, a next imaging protocol is already set by the system control apparatus 130 and the next imaging protocol is the moving image capturing mode (YES in step S308), the processing proceeds to step S309.

In step S309, similar in step S107 of FIG. 4, the imaging control unit 112 determines that the disconnection of the wired communication in step S302 is a temporary one, and maintains the moving image standby state as the moving state of the radiation imaging apparatus 110.

On the other hand, if, as a result of the determination in step S308, there is no next imaging protocol set by the system control apparatus 130 or the next imaging protocol is not the moving image capturing mode (NO in step S308), the processing proceeds to step S310.

In step S310, similar in step S108 of FIG. 4, the imaging control unit 112 sets the power saving standby state, which is a standby state with power consumption lower than that in the moving image capturing state, as the operation state of the radiation imaging apparatus 110 to suppress the consumption of the battery 117.

If the processing of step S309 ends or the processing of step S310 ends, the processing of the flowchart illustrated in FIG. 9 ends.

Figure 10:
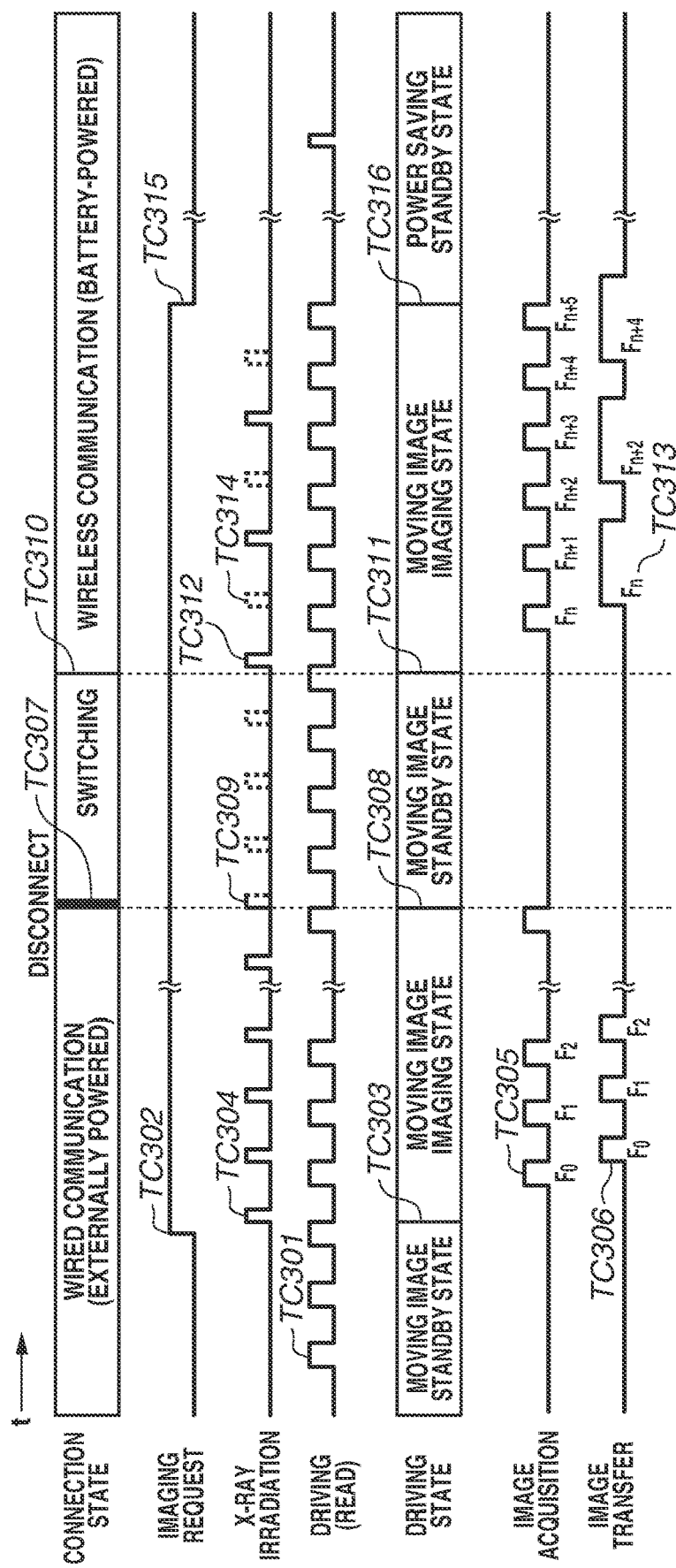
FIG. 10 is a timing chart illustrating an example of a processing procedure of a control method performed in a case where the wired communication with the irradiation communication apparatus is disconnected when the radiation imaging apparatus according to the third exemplary embodiment is in a moving image capturing state.

FIG. 10 is a timing chart illustrating an example of a processing procedure of a control method performed in a case where the wired communication with the irradiation control apparatus 160 is disconnected when the radiation imaging apparatus 110 according to the third exemplary embodiment is in the moving image capturing state. In other words, FIG. 10 is a timing chart corresponding to the processing of the flowchart illustrated in FIG. 9 according to the third exemplary embodiment.

In FIG. 10, the operations up to the detection of the disconnection of the wired communication in the moving image capturing state at TC307 are similar to those up to TC007 in FIG. 6.

In FIG. 10, if the imaging control unit 112 detects the disconnection of the wired communication, the imaging control unit 112 switches the power supply method of the radiation imaging apparatus 110 from the external power supply to the power supply using the battery 117. To switch to wireless communication, the imaging control unit 112 also starts a connection for wireless communication.

During such an operation, the communication between the radiation imaging apparatus 110 and the irradiation control apparatus 160 is completely cut off. Accordingly, the imaging control unit 112 once transitions to the moving image standby state at TC308, and stops radiation irradiation at TC309. At this time, the imaging control unit 112 maintains the cycles of the accumulation and read operations of the radiation detection unit 111 unchanged from those in the moving image capturing state, whereby deterioration in image quality due to valuations of charge accumulation is suppressed. Then, if the switching to the wireless communication is completed at TC310, the imaging control unit 112 restores the operation state to the moving image capturing state at TC311, and starts radiation irradiation in synchronization with the accumulation timing at TC312. The subsequent operations are similar to those of the timing chart of FIG. 8 according to the second exemplary embodiment.

As described above, the radiation imaging apparatus 110 according to the third exemplary embodiment stops radiation irradiation and continues the reading and accumulation operations at constant cycles while switching to the wireless communication after the disconnection of the wired communication. Even if the switching needs a certain time period, the radiation imaging apparatus 110 can thereby perform moving image capturing with stable image quality upon returning to the moving image capturing.

Next, a fourth exemplary embodiment will be described. In the following description of the fourth exemplary embodiment, components similar to those described in the above-described first to third exemplary embodiments are not described. Differences from the above-described first to third exemplary embodiments will be described.

A radiation imaging system according to the fourth exemplary embodiment has a schematic configuration similar to that of the radiation imaging system 100 according to the first exemplary embodiment illustrated in FIG. 1.

In the fourth exemplary embodiment, the operation state of the radiation imaging apparatus 110 is not automatically set based on whether the operation state when the wired communication is disconnected is the moving image capturing state. Instead, whether to continue the moving image capturing state is determined by the user.

Figure 11:
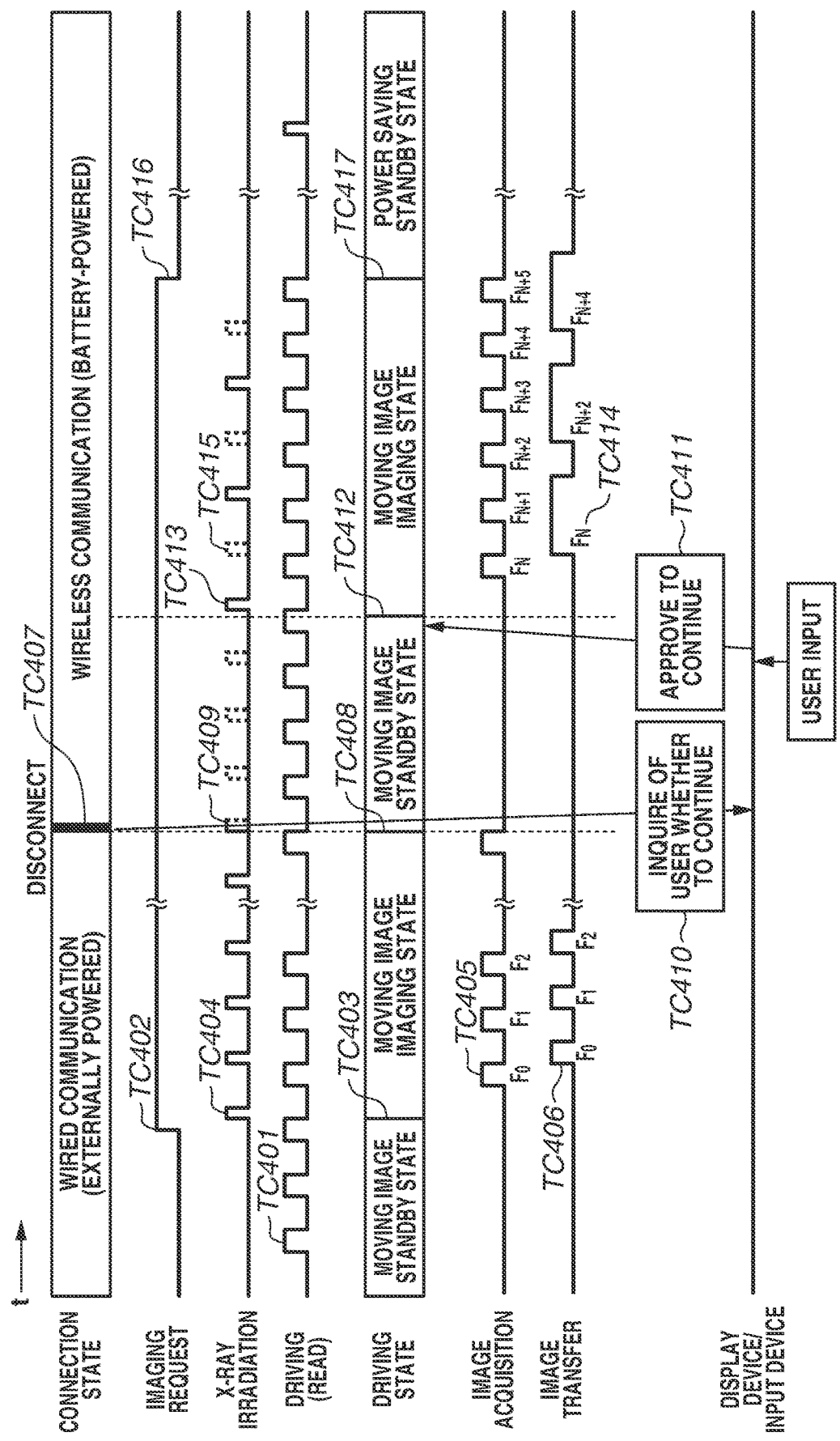
FIG. 11 is a timing chart illustrating an example of a processing procedure of a control method performed in a case where wired communication with an irradiation control apparatus is disconnected when a radiation imaging apparatus according to a fourth exemplary embodiment is in a moving image capturing state.

FIG. 11 is a timing chart illustrating an example of a processing procedure of a control method performed in a case where the wired communication with the irradiation control apparatus 160 is disconnected when the radiation imaging apparatus 110 according to the fourth exemplary embodiment is in the moving image capturing state. In other words, FIG. 11 is a timing chart corresponding to the processing of the flowchart illustrated in FIG. 4 according to the fourth exemplary embodiment, for example.

In FIG. 11, the operations up to the detection of the disconnection of the wired communication in the moving image capturing state at TC407 are similar to those up to TC007 in FIG. 6.

In FIG. 11, if the imaging control unit 112 detects the disconnection of the wired communication, the imaging control unit 112 switches the power supply method of the radiation imaging apparatus 110 from the external power supply to the power supply using the battery 117, and switches to a wireless communication operation. At this time if the operation state is the moving image capturing state, the imaging control unit 112 notifies the system control apparatus 130 of the occurrence of the disconnection of the wired communication during moving image capturing at TC410, for example, by using Ethernet-based command communication.

The system control apparatus 130 notified of the occurrence of the disconnection of the wired communication during moving image capturing displays an inquiry message whether to continue the moving image capturing state by using wireless communication on the display device 150 for user inquiry. During the user inquiry, the imaging control unit 112 makes a setting to temporarily change the operation state of the radiation imaging apparatus 110 to the moving image standby state to avoid ineffective radiation irradiation of the object H. However, the imaging control unit 112 maintains the cycles of the accumulation and read operations of the radiation detection unit 111 unchanged from those in the moving image capturing state at TC408 so that the radiation imaging apparatus 110 can resume moving image capturing with stable image quality upon returning to moving image capturing.

Then, the user inputs an instruction to continue the moving image capturing state from the input device 140. The system control apparatus 130 transmits a continuation notification to the radiation imaging apparatus 110 at TC411. The imaging control unit 112 of the radiation imaging apparatus 110 that has received the continuation notification shifts the operation state of the radiation imaging apparatus 110 to the moving image capturing state, and resumes moving image capturing.

The subsequent processing is similar to that in the timing chart of FIG. 8 according to the second exemplary embodiment. If the user determines not to continue the moving image capturing state, the system control apparatus 130 transmits a stop notification to the radiation imaging apparatus 110. The imaging control unit 112 of the radiation imaging apparatus 110 that has received the stop notification shifts the operation state of the radiation imaging apparatus 110 from the moving image standby state to the power saving standby state.

As described above, if the system control apparatus 130 inquires whether to continue the moving image capturing state after the disconnection of the wired communication, the radiation imaging apparatus 110 according to the fourth exemplary embodiment continues the reading and accumulation operations at constant cycles while radiation irradiation is stopped during inquiry. This enables moving image capturing with stable image quality upon returning to the moving image capturing. Whether to continue moving image capturing when the wired communication is disconnected can be set in advance by the user, for example. In such a case, the inquiry does not need to be made to the user each time the wired communication is disconnected, and whether to continue moving image capturing can be determined based on the information set in advance.

Next, a fifth exemplary embodiment will be described. In the following description of the fifth exemplary embodiment, the description of points similar to the above-described first to fourth exemplary embodiments are omitted. Differences from the above-described first to fourth exemplary embodiments will be described.

The fifth exemplary embodiment deals with a radiation imaging system including a plurality of radiation generation apparatuses 120 (120-1, 120-2), a plurality of irradiation control apparatuses 160 (160-1, 160-2), a plurality of radiation control apparatuses 170 (170-1, 170-2), and a plurality of connection terminals 190 (190-1, 190-2).

Figure 12:
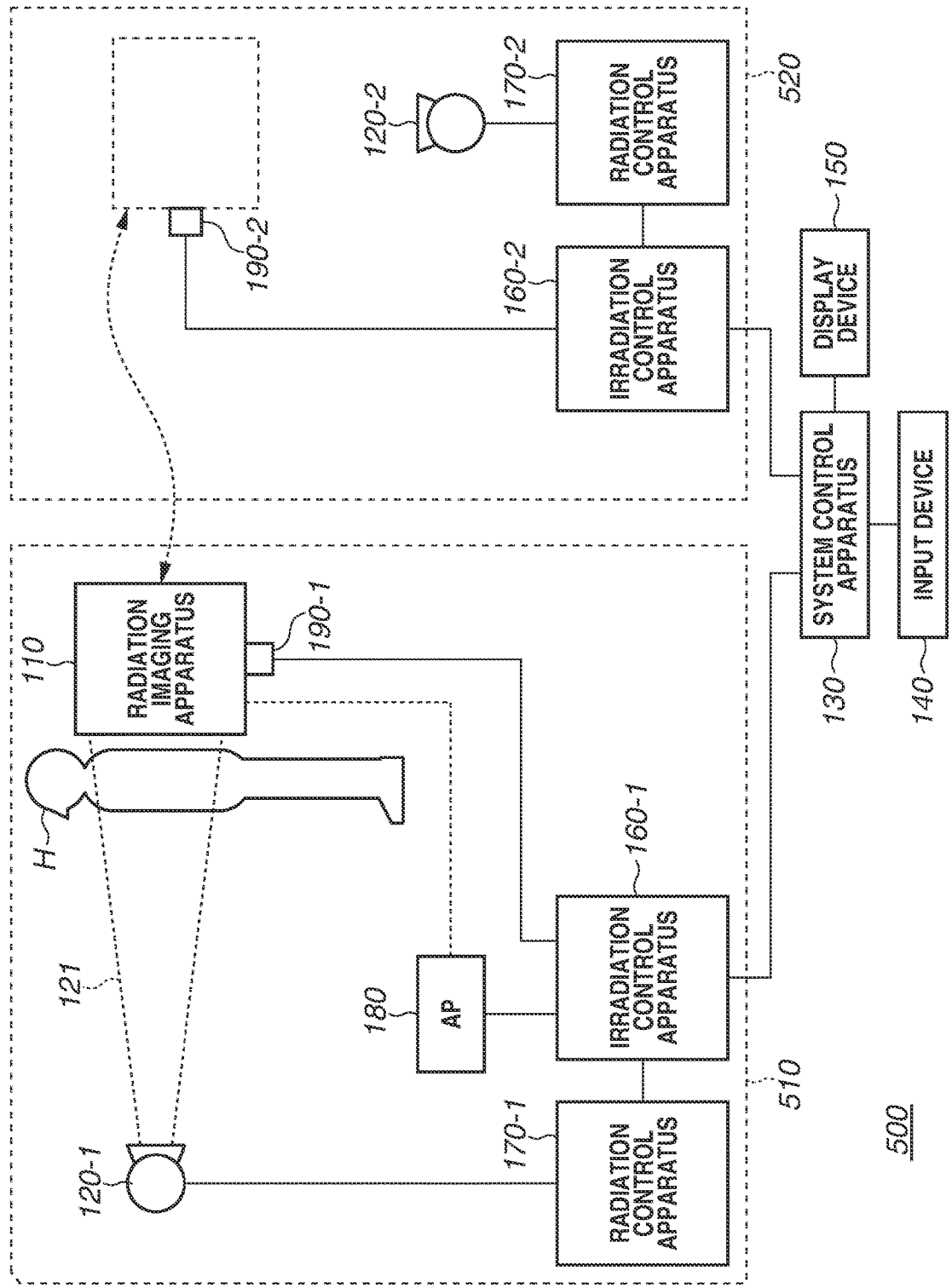
FIG. 12 is a block diagram illustrating an example of a schematic configuration of a radiation imaging system according to a fifth exemplary embodiment.

FIG. 12 is a block diagram schematically illustrating an example of a configuration of a radiation imaging system 500 according to the fifth exemplary embodiment. In FIG. 12, components similar to those of FIG. 1 are designated by the same reference numerals. A detailed description thereof will be omitted.

The radiation imaging system 500 illustrated in FIG. 12 includes component units 120-1, 160-1, 170-1, 180, and 190-1 corresponding to the component units 120, 160, 170, 180, and 190 illustrated in FIG. 1, respectively, in an imaging area 510. The radiation imaging system 500 illustrated in FIG. 12 also includes component units 120-2, 160-2, 170-2, and 190-2 corresponding to the component units 120, 160, 170, and 190 illustrated in FIG. 1, respectively, in an imaging area 520.

In FIG. 12, for example, the radiation imaging apparatus 110 is connected to the irradiation control apparatus 160-1 with a cable via the connection terminal 190-1. To use the radiation imaging apparatus 110 with the irradiation control apparatus 160-2 in another imaging area 520, the radiation imaging apparatus 110 can be once detached from the cable, moved to the imaging area 520, and reconnected to a cable of the irradiation control apparatus 160-2 for moving image capturing.

If the operation state of the radiation imaging apparatus 110 is changed to the power saving standby state by detaching the cable, moving image capturing at high frame rate can fail to be immediately performed when the radiation imaging apparatus 110 is reconnected to the cable of the irradiation control apparatus 160-2. In the radiation imaging system 500 according to the present exemplary embodiment, the system control apparatus 130 then selects the imaging protocol so that the irradiation control apparatus 160-2 can immediately perform moving image capturing at high frame rate, and notifies both the irradiation control apparatus 160-2 and the radiation imaging apparatus 110 to be used of the imaging protocol.

If the imaging protocol or mode to perform moving image capturing is set in advance when the cable is once detached to move the radiation imaging apparatus 110, the imaging control unit 112 of the radiation imaging apparatus 110 sets the moving image standby state. This enables immediate moving image capturing when the radiation imaging apparatus 110 is connected to the cable of the irradiation control apparatus 160-2.

FIG. 13 is a timing chart illustrating an example of a processing procedure of a control method of the radiation imaging apparatus 110 according to the fifth exemplary embodiment.

Suppose that the radiation imaging apparatus 110 is connected to the irradiation control apparatus 160-1 in a wired manner, and is performing the accumulation and reading operations of the radiation detection unit 111 in the moving image standby state at TC501.

Then, at TC502, the system control apparatus 130 selects the imaging protocol so that the irradiation control apparatus 160-2 performs moving image capturing. The system control apparatus 130 notifies the radiation imaging apparatus 110 to set the imaging protocol. If the imaging control unit 112 of the radiation imaging apparatus 110 detects the disconnection of the wired communication in such a state at TC503, the imaging control unit 112 determines that the disconnection is a temporary one since moving image capturing is set as the next imaging protocol. Thus, the imaging control unit 112 maintains the setting of the moving image standby state. At this time, the imaging control unit 112 maintains the preparation state for moving image capturing by maintaining the cycles of the accumulation and reading operations of the radiation detection unit 111 unchanged from before the disconnection of the wired communication. If the imaging control unit 112 detects the connection of the wired communication with the irradiation control apparatus 160-2 in such a state at TC504, the imaging control unit 112 can immediately shift to moving image capturing since the imaging control unit 112 has been prepared in the moving image standby state.

As described above, if the wired communication is disconnected for a temporary movement between the imaging areas, the radiation imaging apparatus 110 according to the fifth exemplary embodiment can reduce preparation time to make stable moving image capturing available at the destination.

In the first to fifth exemplary embodiments described above, the configurations of the radiation imaging systems, moving image standby operations, moving image capturing operations, and operation setting methods performed when the wired communication is disconnected have been described. In any of the methods, the moving image standby state or the moving image capturing state is set if the disconnection of the wired communication is determined to be a temporary one or an unintentional one. This enables appropriate moving image capturing with higher convenience, for example, by enabling continuation of the moving image capturing state at the time of an unintended disconnection and enabling a reduction in preparation time to make stable moving image capturing available when the wired communication is reconnected.

Other Exemplary Embodiments

Exemplary embodiments can be implemented by processing of supplying a program implementing one or more functions of the above-described exemplary embodiments to a system or an apparatus via a network or a storage medium, and of reading and executing the program by one or more processors of a computer of the system or apparatus. A circuit implementing one or more functions (e.g., application specific integrated circuit (ASIC)) can be used for implementation.

The program and a computer-readable storage medium storing such a program are included in the scope of the present disclosure.

All the above-described exemplary embodiments are merely illustrative of implementation examples, and should not be interpreted to limit the technical scope of the present disclosure. In other words, the present disclosure can be realized in various forms without departing from the technical concept or main features thereof.

Other Embodiments

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2018-045449, filed Mar. 13, 2018, which is hereby incorporated by reference herein in its entirety.

What is claimed is:

1. A radiation imaging apparatus configured to perform wired communication with an external apparatus, the radiation imaging apparatus comprising:
    a radiation detection unit configured to detect incident radiation and obtain a moving image related to the radiation; and
    an imaging control unit configured to perform control to, in a first case where the wired communication is disconnected in a moving image capturing state in which the moving image is captured, set the moving image capturing state, and in a second case where the wired communication is disconnected not in the moving image capturing state and moving image capturing is set as next imaging, set a moving image standby state, the moving image standby state being a standby state for the moving image capturing.

2. The radiation imaging apparatus according to claim 1, wherein the imaging control unit is configured to, if the moving image standby state is set, perform control to stop generation of the radiation, and perform control to cause a time for the radiation detection unit to obtain each frame constituting the moving image with substantially the same power consumption as in the moving image capturing state to be substantially the same as in the moving image capturing state.

3. The radiation imaging apparatus according to claim 1, further configured to perform wireless communication with the external apparatus,
    wherein the imaging control unit is configured to, if a wireless connection with the external apparatus by the wireless communication is completed in the first case, perform control to set the moving image capturing state.

4. The radiation imaging apparatus according to claim 3, wherein the imaging control unit is configured to perform control to, if the wireless connection is not yet completed in the first case, set the moving image standby state, and if the wireless connection is completed thereafter, set the moving image capturing state.

5. The radiation imaging apparatus according to claim 3, further comprising a wireless communication unit configured to, if the wireless connection with the external apparatus by the wireless communication is completed in the first case, transmit each frame constituting the moving image to the external apparatus via the wireless communication.

6. The radiation imaging apparatus according to claim 5, further comprising a storage unit configured to, if a time for the wireless communication unit to transmit each frame constituting the moving image to the external apparatus is longer than a time for the radiation detection unit to obtain each frame, store any frames unable to be transmitted on time.

7. The radiation imaging apparatus according to claim 6, wherein the wireless communication unit is configured to, if shifting to a state other than the moving image capturing state, transmit the frames stored in the storage unit to the external apparatus.

8. The radiation imaging apparatus according to claim 7, wherein the imaging control unit is configured to, in a third case where the wired communication is disconnected not in the moving image capturing state and the moving image capturing is not set as the next imaging, perform control to set a power saving standby state where power consumption is lower than power consumption in the moving image capturing state, and
    wherein the wireless communication unit is configured to, if shifting to the power saving standby state, transmit the frames stored in the storage unit to the external apparatus.

9. The radiation imaging apparatus according to claim 7, wherein the wireless communication unit is configured to, if shifting to the moving image standby state, transmit the frames stored in the storage unit to the external apparatus.

10. The radiation imaging apparatus according to claim 5, wherein the imaging control unit is configured to, if the moving image capturing state is set and the time for the wireless communication unit to transmit each frame constituting the moving image to the external apparatus is longer than the time for the radiation detection unit to obtain each frame, perform control to stop generation of the radiation to be generated by a radiation generation apparatus to obtain the frame unable to be transmitted on time.

11. The radiation imaging apparatus according to claim 1, wherein the radiation imaging unit is configured to, if the wired communication is not disconnected, operate the radiation detection unit by using a power supply of the external apparatus, and if the wired communication is disconnected, operate the radiation detection unit by using a power supply of the radiation imaging apparatus.

12. A radiation imaging system, comprising:
the radiation imaging apparatus according to claim 1;
a radiation generation apparatus configured to generate the radiation;
the external apparatus configured to communicate with the radiation imaging apparatus and receive the moving image from the radiation imaging apparatus; and
a system control apparatus configured to communicate with the external apparatus and perform control to receive the moving image from the external apparatus and display the moving image on a display device.

13. A method for controlling a radiation imaging apparatus configured to perform wired communication with an external apparatus, the radiation imaging apparatus including a radiation detection unit configured to detect an incident radiation and obtain a moving image related to the radiation, the method comprising:
performing control, in a first case where the wired communication is disconnected in a moving image capturing state in which the moving image is captured, to set the moving image capturing state; and
performing control, in a second case where the wired communication is disconnected not in the moving image capturing state and moving image capturing is set as next imaging, to set a moving image standby state, the moving image standby state being a standby state for the moving image capturing.

14. A storage medium storing a program for causing a computer to perform a method for controlling a radiation imaging apparatus configured to perform wired communication with an external apparatus, the radiation imaging apparatus including a radiation detection unit configured to detect incident radiation and obtain a moving image related to the radiation, the method comprising:
performing control, in a first case where the wired communication is disconnected in a moving image capturing state in which the moving image is captured, to set the moving image capturing state; and
performing control, in a second case where the wired communication is disconnected not in the moving image capturing state and moving image capturing is set as next imaging, to set a moving image standby state, the moving image standby state being a standby state for the moving image capturing.

* * * * *